(12) United States Patent
Aoyama

(10) Patent No.: US 10,842,366 B2
(45) Date of Patent: Nov. 24, 2020

(54) ENDOSCOPE SYSTEM

(71) Applicant: FUJIFILM Corporation, Tokyo (JP)

(72) Inventor: Tatsuya Aoyama, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 72 days.

(21) Appl. No.: 16/383,674

(22) Filed: Apr. 15, 2019

(65) Prior Publication Data
US 2019/0239736 A1 Aug. 8, 2019

Related U.S. Application Data

(63) Continuation of application No. PCT/JP2017/033113, filed on Sep. 13, 2017.

(30) Foreign Application Priority Data

Oct. 27, 2016 (JP) .................................. 2016-211058

(51) Int. Cl.
*G06K 9/00* (2006.01)
*A61B 1/06* (2006.01)
(Continued)

(52) U.S. Cl.
CPC .............. *A61B 1/0638* (2013.01); *A61B 1/00* (2013.01); *A61B 1/00004* (2013.01);
(Continued)

(58) Field of Classification Search
None
See application file for complete search history.

(56) References Cited

U.S. PATENT DOCUMENTS

2004/0059215 A1  3/2004 Nishimura et al.
2009/0021578 A1*  1/2009 Yamazaki .............. H04N 5/217
                                                        348/65
(Continued)

FOREIGN PATENT DOCUMENTS

EP  3520676  8/2019
EP  3524132  8/2019

OTHER PUBLICATIONS

"Search Report of Europe Counterpart Application", dated Oct. 31, 2019, p. 1-p. 8.

*Primary Examiner* — Hadi Akhavannik
(74) *Attorney, Agent, or Firm* — JCIPRNET

(57) ABSTRACT

An endoscope system capable of setting the optimal balance of light source wavelengths in accordance with a diagnosis purpose is provided. An endoscope system includes a diagnosis purpose acquisition unit, a plurality of light sources with different light emission wavelengths, a light quantity ratio storage unit, a light quantity ratio selection unit, and a light source control unit. The diagnosis purpose acquisition unit acquires a diagnosis purpose. The light quantity ratio storage unit stores correspondence between the diagnosis purpose and a plurality of light quantity ratios with different balances of respective emission light quantities of the plurality of light sources. The light quantity ratio selection unit refers to the light quantity ratio storage unit and selects the light quantity ratio that is used for the acquired diagnosis purpose. The light source control unit controls the plurality of light sources to emit illumination light with the selected light quantity ratio.

16 Claims, 21 Drawing Sheets

(51) Int. Cl.
*A61B 1/00* (2006.01)
*A61B 1/045* (2006.01)

(52) U.S. Cl.
CPC ...... *A61B 1/00039* (2013.01); *A61B 1/00045* (2013.01); *A61B 1/045* (2013.01); *A61B 1/06* (2013.01)

(56) References Cited

U.S. PATENT DOCUMENTS

| | | | |
|---|---|---|---|
| 2009/0315985 A1* | 12/2009 | Hirano | A61B 1/042 348/65 |
| 2011/0237894 A1* | 9/2011 | Ozawa | A61B 1/043 600/168 |
| 2012/0013773 A1* | 1/2012 | Yoshino | G06T 7/32 348/241 |
| 2012/0116159 A1* | 5/2012 | Mizuyoshi | A61B 1/0638 600/109 |
| 2012/0190922 A1 | 7/2012 | Kaku | |
| 2013/0294674 A1* | 11/2013 | Miyamoto | G06T 7/0014 382/132 |
| 2014/0152790 A1* | 6/2014 | Saito | A61B 1/0005 348/68 |
| 2014/0316283 A1* | 10/2014 | Kaku | A61B 1/0638 600/479 |
| 2015/0335232 A1* | 11/2015 | Ito | A61B 1/07 362/13 |

\* cited by examiner

FIG. 5

68 — LIGHT QUANTITY RATIO STORAGE UNIT

68a

| FIRST DIAGNOSIS PURPOSE | LIGHT QUANTITY RATIO |
|---|---|
| LARGE INTESTINE SCREENING | R11 |
|  | R12 |
| STOMACH SCREENING | R13 |
| LARGE INTESTINE CLOSE INSPECTION | R14 |

68b

| SECOND DIAGNOSIS PURPOSE | LIGHT QUANTITY RATIO |
|---|---|
| BARRETT'S ESOPHAGUS | R21 |
|  | R22 |
| LARGE INTESTINAL POLYPOSIS | R23 |
| ANGIODYSPLASIA | R24 |

68c

| THIRD DIAGNOSIS PURPOSE | LIGHT QUANTITY RATIO |
|---|---|
| REMISSION PERIOD OF ULCERATIVE COLITIS | R31 |
|  | R32 |
| ACTIVE PERIOD OF ULCERATIVE COLITIS | R33 |

FIG. 14

104 INDEX VALUE STORAGE UNIT

104a

| FIRST DIAGNOSIS PURPOSE | INDEX VALUE |
|---|---|
| LARGE INTESTINE SCREENING | COMPLEXITY OF SURFACE LAYER BLOOD VESSEL |
| | COMPLEXITY OF MIDDLE LAYER BLOOD VESSEL |
| STOMACH SCREENING | COMPLEXITY OF MIDDLE LAYER BLOOD VESSEL |
| | UNIFORMITY OF SURFACE STRUCTURE |
| LARGE INTESTINE CLOSE INSPECTION | DENSITY OF SURFACE LAYER BLOOD VESSEL |

104b

| SECOND DIAGNOSIS PURPOSE | INDEX VALUE |
|---|---|
| BARRETT'S ESOPHAGUS | DENSITY OF SURFACE LAYER BLOOD VESSEL |
| | COMPLEXITY OF SURFACE LAYER BLOOD VESSEL |
| | DENSITY OF MIDDLE LAYER BLOOD VESSEL |
| | COMPLEXITY OF MIDDLE LAYER BLOOD VESSEL |
| LARGE INTESTINAL POLYPOSIS | UNIFORMITY OF THICKNESS OF MIDDLE LAYER BLOOD VESSEL |
| | UNIFORMITY OF SURFACE STRUCTURE |
| ANGIODYSPLASIA | DENSITY OF MIDDLE LAYER BLOOD VESSEL |

104c

| THIRD DIAGNOSIS PURPOSE | INDEX VALUE |
|---|---|
| REMISSION PERIOD OF ULCERATIVE COLITIS | COMPLEXITY OF SURFACE LAYER BLOOD VESSEL |
| | COMPLEXITY OF MIDDLE LAYER BLOOD VESSEL |
| ACTIVE PERIOD OF ULCERATIVE COLITIS | COMPLEXITY OF SURFACE LAYER BLOOD VESSEL |

FIG. 19

122 INDEX VALUE STORAGE UNIT

122a

| FIRST DIAGNOSIS PURPOSE | INDEX VALUE | COEFFICIENT |
|---|---|---|
| LARGE INTESTINE SCREENING | COMPLEXITY OF SURFACE LAYER BLOOD VESSEL | 0.5 |
| | COMPLEXITY OF MIDDLE LAYER BLOOD VESSEL | 1 |
| STOMACH SCREENING | COMPLEXITY OF MIDDLE LAYER BLOOD VESSEL | 1 |
| | UNIFORMITY OF SURFACE STRUCTURE | 1 |
| LARGE INTESTINE CLOSE INSPECTION | DENSITY OF SURFACE LAYER BLOOD VESSEL | 1 |

122b

| SECOND DIAGNOSIS PURPOSE | INDEX VALUE | COEFFICIENT |
|---|---|---|
| BARRETT'S ESOPHAGUS | DENSITY OF SURFACE LAYER BLOOD VESSEL | 1 |
| | COMPLEXITY OF SURFACE LAYER BLOOD VESSEL | 1 |
| | DENSITY OF MIDDLE LAYER BLOOD VESSEL | 1 |
| | COMPLEXITY OF MIDDLE LAYER BLOOD VESSEL | 1 |
| LARGE INTESTINAL POLYPOSIS | UNIFORMITY OF THICKNESS OF MIDDLE LAYER BLOOD VESSEL | 1 |
| | UNIFORMITY OF SURFACE STRUCTURE | 0.5 |
| ANGIODYSPLASIA | DENSITY OF MIDDLE LAYER BLOOD VESSEL | 1 |

122c

| THIRD DIAGNOSIS PURPOSE | INDEX VALUE | COEFFICIENT |
|---|---|---|
| REMISSION PERIOD OF ULCERATIVE COLITIS | COMPLEXITY OF SURFACE LAYER BLOOD VESSEL | 1 |
| | COMPLEXITY OF MIDDLE LAYER BLOOD VESSEL | 1 |
| ACTIVE PERIOD OF ULCERATIVE COLITIS | COMPLEXITY OF SURFACE LAYER BLOOD VESSEL | 1 |

ENDOSCOPE SYSTEM

CROSS REFERENCE TO RELATED APPLICATIONS

This application is a Continuation of PCT International Application No. PCT/JP2017/033113 filed on Sep. 13, 2017, which claims priority under 35 U.S.C § 119(a) to Patent Application No. 2016-211058 filed in Japan on Oct. 27, 2016, all of which are hereby expressly incorporated by reference into the present application.

BACKGROUND OF THE INVENTION

1. Field of the Invention

The present invention relates to an endoscope system.

2. Description of the Related Art

In medical fields, diagnoses using an endoscope system including a light source device, an endoscope, and a processor device are being widely performed. With an endoscope system, an observation object is irradiated with illumination light emitted by a light source device via an endoscope, an image signal is obtained by image-capturing the observation object illuminated with the illumination light, and a processor device generates an image of the observation object on the basis of the image signal. By displaying the image on a monitor, a doctor can make a diagnosis while watching the image on the monitor.

Also in endoscopic diagnoses in recent years, as described in WO2010/116902A and JP2011-036361A, the balance of light source wavelengths is being switched in accordance with an observation portion or observation magnification for visualization. With WO2010/116902A and JP2011-036361A, to observe a surface layer blood vessel in a close view and to perform overall observation with a hue of white light in a distant view, illumination is provided by using light with short wavelengths in a close view and illumination is provided by using white light in a distant view. For example, as described in JP2013-017769A, JP2015-061618A, and JP2015-231576A, the balance of light source wavelengths is being changed in accordance with an observation portion.

Furthermore, in endoscopic diagnoses in recent years, as described in JP2012-080939A and JP2016-087370A, a diagnosis assisting system is being introduced to fill a difference in skill among doctors. The diagnosis assisting system extracts a feature of a lesion portion from an image obtained by imaging an observation object, indexes the feature, and displays the index.

SUMMARY OF THE INVENTION

Endoscopic diagnoses handle various subject diseases, diagnosis purposes, and stages of diseases to be inspected. Hence it is desirable to set the balance of light source wavelengths to the balances optimal for such subject diseases and so forth. That is, light with short wavelengths in a close view or white light in a distant view may not occasionally has the optimal balances of light source wavelengths for a certain subject disease. In addition, the optimal balance of light source wavelengths may vary even for the same observation portion. For example, for the same large intestine, there are cases in which "a blood vessel transparent image is observed by using light with short wavelengths for screening" and "the degree of integration of deep blood vessels is observed by using light with long wavelengths for observing ulcerative colitis". In this way, the optimal balance of light source wavelengths varies in accordance with the purpose even for the same portion.

In addition, to introduce the diagnosis assisting system that uses indexing, it is important to set the light source balance suitable for plotting and distinguishing a feature structure of a lesion portion.

An object of the present invention is to provide an endoscope system capable of setting the optimal balance of light source wavelengths in accordance with the diagnosis purpose.

An endoscope system according to the present invention includes a diagnosis purpose acquisition unit that acquires a diagnosis purpose; a plurality of light sources with different light emission wavelengths; a light quantity ratio storage unit that stores correspondence between the diagnosis purpose and a plurality of light quantity ratios with different balances of respective emission light quantities of the plurality of light sources; a light quantity ratio selection unit that refers to the light quantity ratio storage unit and selects a light quantity ratio that is used for the acquired diagnosis purpose; and a light source control unit that controls the plurality of light sources to emit illumination light with the selected light quantity ratio.

The diagnosis purpose includes a first diagnosis purpose including screening and close inspection, a second diagnosis purpose relating to a type of disease, and a third diagnosis purpose relating to a stage of disease. Preferably, the light quantity ratio selection unit selects the light quantity ratio in accordance with a combination of the first to third diagnosis purposes, or the light quantity ratio selection unit selects the light quantity ratio in accordance with one diagnosis purpose of the first to third diagnosis purposes.

Preferably, the endoscope system further includes an image generation unit that generates an image by using an image signal that is obtained by an endoscope image-capturing an observation object illuminated with the illumination light; and an image storage unit that stores the image in association with at least one of the acquired diagnosis purpose or the selected light quantity ratio.

Preferably, the endoscope system further includes an index value storage unit that stores correspondence between the diagnosis purpose and a plurality of index values relating to a structure of the observation object; an index value selection unit that selects an index value that is used for the acquired diagnosis purpose, from among the index values stored in the index value storage unit; and an index value calculation unit that uses the image and calculates the selected index value.

Preferably, the image generation unit uses the calculated index value and generates, as the image, an image in which the structure is displayed in an emphasized manner.

Preferably, the endoscope system further includes a structure parameter calculation unit that calculates a structure parameter of the structure by weighting a plurality of the index values with a weighting coefficient determined in accordance with the diagnosis purpose and arithmetically operating the index values.

Preferably, the image generation unit uses the calculated structure parameter and generates, as the image, an image in which the structure is displayed in an emphasized manner.

Preferably, the image storage unit stores the image further in association with the calculated structure parameter.

Preferably, the endoscope system is connected to an endoscope information management system having a data storage unit that stores endoscope information management data including the diagnosis purpose so as to mutually communicate with each other through a network, and the diagnosis purpose acquisition unit receives the endoscope information management data through the network, and acquires the diagnosis purpose by extracting the diagnosis purpose from the received endoscope information management data.

Preferably, the endoscope system further includes a diagnosis purpose input unit that inputs the diagnosis purpose, and the diagnosis purpose acquisition unit acquires the diagnosis purpose input by the diagnosis purpose input unit.

An endoscope system according to the present invention includes a diagnosis purpose acquisition unit that acquires a diagnosis purpose; a plurality of light sources with different light emission wavelengths; a light quantity ratio storage unit that stores correspondence between the diagnosis purpose and a plurality of light quantity ratios with different balances of respective emission light quantities of the plurality of light sources; a light quantity ratio selection unit that refers to the light quantity ratio storage unit and selects a light quantity ratio that is used for the acquired diagnosis purpose; a light source control unit that controls the plurality of light sources to emit illumination light with the selected light quantity ratio; an image generation unit that generates an image by using an image signal that is obtained by an endoscope image-capturing an observation object illuminated with the illumination light; and a display unit that displays the image. The endoscope system is connected to an endoscope information management system having a data storage unit that stores endoscope information management data including the diagnosis purpose so as to mutually communicate with each other through a network. The diagnosis purpose acquisition unit receives the endoscope information management data through the network, and acquires the diagnosis purpose by extracting the diagnosis purpose from the received endoscope information management data.

With the endoscope system of the present invention, the optimal balance of light source wavelengths can be set in accordance with the diagnosis purpose.

BRIEF DESCRIPTION OF THE DRAWINGS

FIG. 5 is an illustration explaining a light quantity ratio storage unit;

FIG. 14 is an illustration explaining an index value storage unit;

FIG. 19 is an illustration explaining an index value storage unit according to the third embodiment;

DESCRIPTION OF THE PREFERRED EMBODIMENTS

First Embodiment

Figure 1:
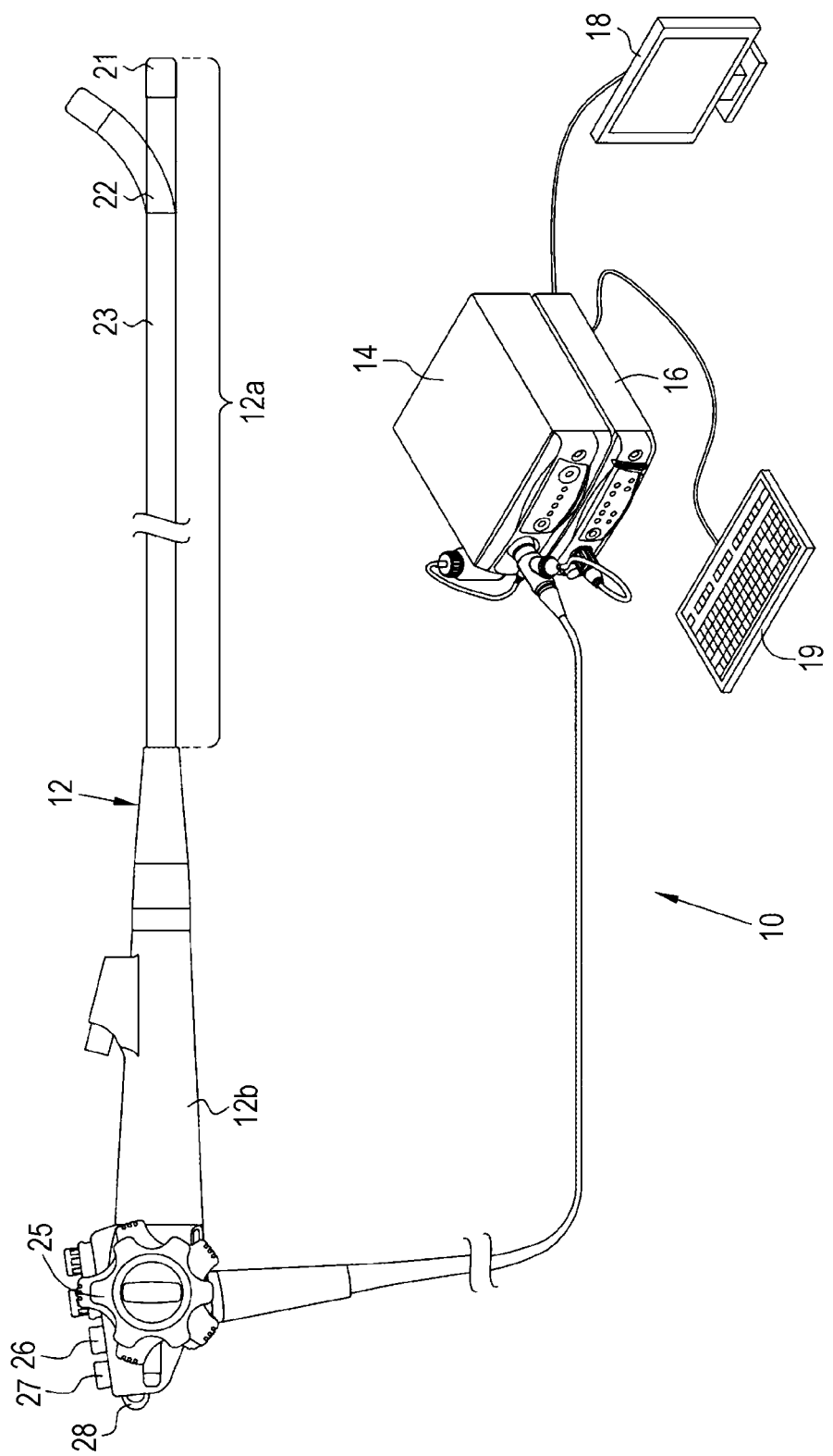
FIG. 1 is an external view of an endoscope system according to a first embodiment.

As illustrated in FIG. 1, an endoscope system 10 has an endoscope 12, a light source device 14, a processor device 16, a display unit 18, and an instruction input part 19. The endoscope 12 image-captures an observation portion in a living body serving as a subject. The light source device 14 supplies illumination light that illuminates the observation portion, to the endoscope 12. The processor device 16 generates a display image of the observation portion by using an image pick-up signal obtained by image-capturing. The display unit 18 is a monitor that displays a display image and information and so forth accompanying the display image. The instruction input part 19 is a console of a keyboard, a mouse, and so forth, and functions as a user interface that receives input operations, such as designation of a region of interest (ROI) and functional setting. The display unit 18 and the instruction input part 19 are electrically connected to the processor device 16.

The endoscope 12 is optically connected to the light source device 14, and is electrically connected to the processor device 16. The endoscope 12 has an insertion section 12a and an operation section 12b.

The insertion section 12a is a section that is inserted into an alimentary canal or the like of the living body. The insertion section 12a has a distal end portion 21, a bending portion 22, and a flexible pipe portion 23 that are coupled in that order from the distal end side. The distal end portion 21 has, at a distal end surface, an illumination window, an observation window, an air/water supply nozzle, and a forceps port (none of these is illustrated). The illumination window is for irradiating the observation portion with the illumination light. The observation window is for taking in the light from the observation portion. The air/water supply nozzle is for washing the illumination window and the observation window. The forceps port is for performing various treatments using treatment tools, such as a pair of forceps and an electric scalpel. The bending portion 22 is constituted by coupling a plurality of bending pieces, and bends in up-down and left-right directions. The flexible pipe portion 23 is flexible, and can be inserted into a bending tubular path, such as the esophagus or intestine.

The operation section 12b has an angle knob 25, an image storage operating unit 26, a mode switching unit 27, and a zoom operating unit 28. The angle knob 25 is used for an operation of bending the bending portion 22 so as to direct the distal end portion 21 in a desirable direction. The image storage operating unit 26 is used for an operation of storing a still image and/or a movie in a storage (not illustrated). The mode switching unit 27 is used for an operation of switching an observation mode. The zoom operating unit 28 is used for an operation of changing zoom magnification.

The endoscope system 10 has, as operation modes, a normal observation mode, a special observation mode, and a suitable object observation mode. In the normal observation mode, an image in which an observation object with natural colors is captured (hereinafter, referred to as normal observation image) is acquired. In the special observation mode, an image in which a blood vessel that is an observation object is at least emphasized (hereinafter, referred to as special observation image) is acquired. In the suitable object observation mode, an image in which a structure that is an observation object suitable for the diagnosis purpose is emphasized (hereinafter, referred to as suitable object observation image) is acquired. In this embodiment, a structure includes a structure of a blood vessel and a structure of a gland duct (pit pattern). In the following description, when a structure of a blood vessel and a structure of a gland duct are not distinguished from each other, these structures each are referred to as a structure.

Figure 2:
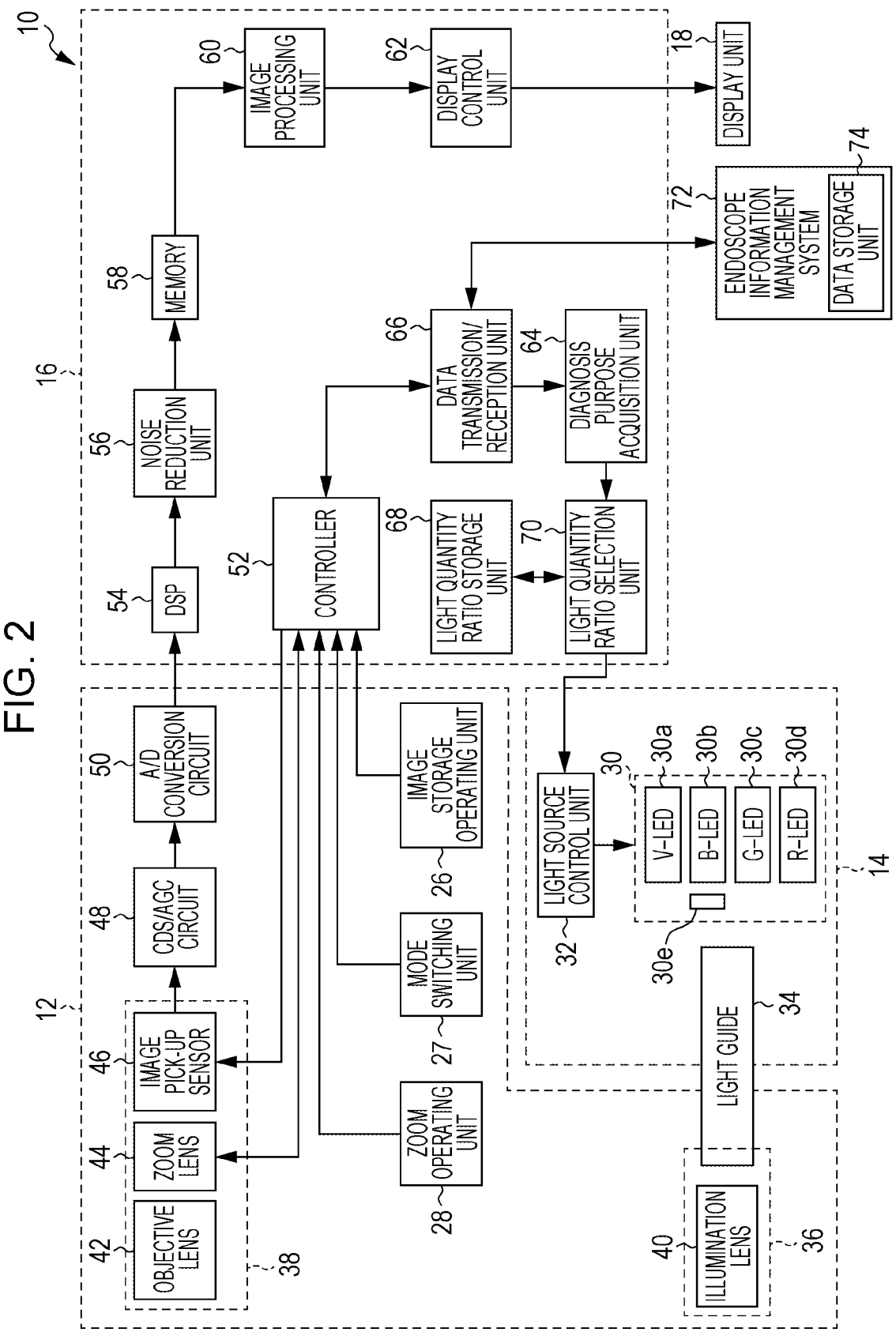
FIG. 2 is a block diagram illustrating a function of the endoscope system.

As illustrated in FIG. 2, the light source device 14 includes a light source 30 that emits illumination light, and a light source control unit 32 that controls the light source 30. The light source 30 is, for example, a semiconductor light source such as light emitting diodes (LEDs) of a plurality of colors with different wavelength ranges.

In this embodiment, the light source 30 has, for example, four-color LEDs of a violet light emitting diode (V-LED) 30a, a blue light emitting diode (B-LED) 30b, a green light emitting diode (G-LED) 30c, and a red light emitting diode (R-LED) 30d. The V-LED 30a emits light with light emission wavelengths in a range of from 380 nm to 420 nm. The B-LED 30b emits light with light emission wavelengths in a range of from 420 nm to 500 nm. The G-LED 30c emits light with light emission wavelengths in a range of from 480 nm to 600 nm. The R-LED 30d emits light with light emission wavelengths in a range of from 600 nm to 650 nm. The lights of the respective colors may each have the same central wavelength and peak wavelength, or may have different central wavelength and peak wavelength.

The light source 30 includes an optical filter 30e that adjusts the wavelength range of light emitted from a LED. In this embodiment, the optical filter 30e is arranged on the optical path of the B-LED 30b, and transmits a short wavelength component included in the wavelength range of the B-LED 30b. To be specific, the optical filter 30e transmits light of 450 nm or shorter included in the wavelength range of the B-LED 30b. A long wavelength component included in the wavelength range of the B-LED 30b decreases the contrast between a mucous membrane and a blood vessel. Thus, by using the optical filter 30e, the short wavelength component included in the wavelength range of the B-LED 30b is supplied to a light guide 34 (described later). The optical filter 30e is arranged on the optical path of the B-LED 30b in this embodiment; however, it is not limited thereto. For example, the optical filter 30e may be arranged on the optical path of the G-LED 30c. The wavelength component to be transmitted by the optical filter 30e can be appropriately set. For example, when the optical filter 30e is arranged on the optical path of the G-LED 30c, the optical filter 30e transmits part of the wavelength range of the G-LED 30c.

The light source control unit 32 adjusts the light emitting timing, light emitting duration, light quantity, and spectrum of illumination light of each of the LEDs 30a to 30d by independently controlling turning ON or OFF of each of the LEDs 30a to 30d, and the balance of respective emission light quantities of the LEDs 30a to 30d (hereinafter, referred to as light quantity ratio). In this embodiment, the light source control unit 32 controls the light quantity ratio of the LEDs 30a to 30d on an observation mode basis by adjusting the electric current and voltage for driving each of the LEDs 30a to 30d.

Figure 3:
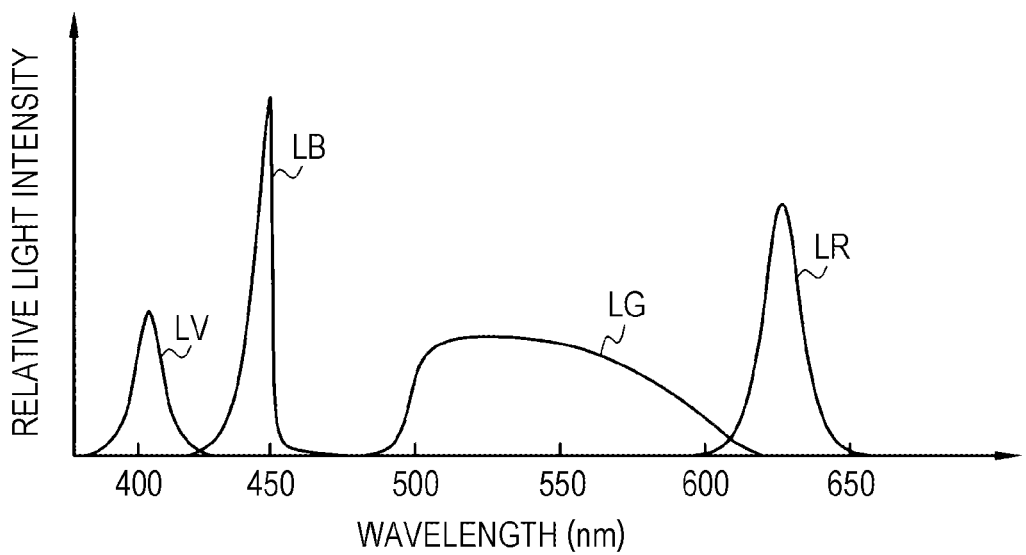
FIG. 3 illustrates a light intensity spectrum of illumination light in a normal observation mode.

As illustrated in FIG. 3, in the normal observation mode, the light source control unit 32 turns ON all the LEDs 30a to 30d, and hence almost white illumination light (hereinafter, referred to as white light) including violet light LV emitted from the V-LED 30a, blue light LB emitted from the B-LED 30b, green light LG emitted from the G-LED 30c, and red light LR emitted from the R-LED 30d is emitted. In this embodiment, the blue light LB is light transmitted through the optical filter 30e, that is, light of 450 nm or shorter included in the wavelength range of the B-LED 30b.

Figure 4:
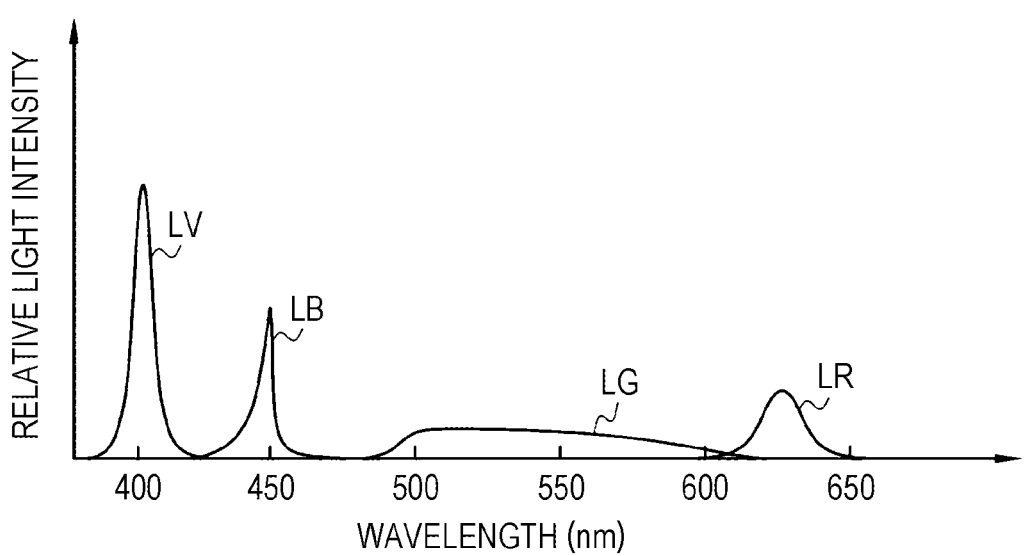
FIG. 4 illustrates a light intensity spectrum of illumination light in a special observation mode.

As illustrated in FIG. 4, in the special observation mode, the light source control unit 32 causes illumination light to be emitted such that the emission light quantity of the V-LED 30a is larger than that in the normal observation mode and the respective emission light quantities of the B-LED 30b, G-LED 30c, and R-LED 30d are smaller than those in the normal observation mode. The violet light LV is light in a wavelength range that is optimal for observing a surface layer blood vessel located at a shallow position from a mucous membrane surface.

In the case of the suitable object observation mode, the light source control unit 32 controls light emission of the LEDs 30a to 30d in accordance with the light quantity ratio determined in accordance with the diagnosis purpose acquired by a diagnosis purpose acquisition unit 64 (described later). Although light emission control in the suitable object observation mode is described later in detail, the light quantity ratio with which the structure suitable for the diagnosis purpose can be observed is selected by a light quantity ratio selection unit 70 (described later), and the light source control unit 32 emits illumination light with the selected light quantity ratio. For example, when the blood vessel suitable for the acquired diagnosis purpose is a surface layer blood vessel, the light source control unit 32 turns ON only the V-LED 30a among the LEDs 30a to 30d to emit violet light LV. In addition, there may be a case where a middle layer blood vessel at a deeper position than the position of a surface layer blood vessel may be focused in accordance with the diagnosis purpose. In this case, the light source control unit 32 turns ON only the B-LED 30b among the LEDs 30a to 30d to emit blue light LB. The way of light emission is not limited to emitting only the violet light LV or emitting only the blue light LB. For example, the violet light LV and the blue light LB may be sequentially emitted. Further, illumination light including the violet light LV and the blue light LB, illumination light consisting of only green light LG, illumination light consisting of only red light LR, illumination light including the violet light LV and the red light LR, illumination light including the blue light LB and the red light LR, and so forth, may be emitted.

The illumination light emitted from the light source 30 is incident on the light guide 34 inserted through the insertion section 12a. The light guide 34 is embedded in the endoscope 12 and a universal cord. Illumination light propagates through the light guide 34 to the distal end portion 21 of the endoscope 12. The universal cord is a cord that connects the endoscope 12, the light source device 14, and the processor device 16 to one another. For the light guide 34, a multi-mode fiber can be used. For example, for the light guide 34, a small-diameter fiber cable having a core diameter of 105 μm, a cladding diameter of 125 μm, and a diameter including a protective layer serving as an outer cover in a range of from φ0.3 to 0.5 mm can be used.

The distal end portion 21 has an illumination optical system 36 and an image pick-up optical system 38. The illumination optical system 36 has an illumination lens 40. The illumination light propagating through the light guide 34 illuminates an observation object via the illumination lens 40. The image pick-up optical system 38 has an objective lens 42, a zoom lens 44, and an image pick-up sensor 46. Various lights, such as reflected light, scattered light, and fluorescence, from the observation object are incident on the image pick-up sensor 46 via the objective lens 42 and the zoom lens 44. Thus, an image of the observation object is formed on the image pick-up sensor 46. The zoom lens 44 freely moves between the telephoto end and the wide end by operating the zoom operating unit 28, to enlarge or contract the image of the observation object formed on the image pick-up sensor 46.

The image pick-up sensor 46 is a color image pick-up sensor provided with a color filter of one of primary colors of red (R), green (G), and blue (B) for each pixel, image-captures the observation object, and outputs an image signal of corresponding one of RGB. For the image pick-up sensor 46, a charge coupled device (CCD) image pick-up sensor, a complementary metal-oxide semiconductor (CMOS) image pick-up sensor, or the like, can be used. Alternatively, instead of the image pick-up sensor 46 provided with the color filters of the primary colors, a complementary-color image pick-up sensor including complementary-color filters of cyan (C), magenta (M), yellow (Y), and green (G) may be used. When the complementary-color image pick-up sensor is used, image signals of four colors of CMYG are output. By converting the image signals of the four colors of CMYG into the image signals of the three colors of RGB by color conversion from complementary colors to primary colors, image signals of the respective colors of RGB similar to those of the image pick-up sensor 46 can be obtained. Instead of the image pick-up sensor 46, a monochrome sensor without a color filter may be used.

A correlated double sampling (CDS)/automatic gain control (AGC) circuit 48 performs correlative double sampling and automatic gain control on an analog image signal output from the image pick-up sensor 46. An analog to digital (A/D) conversion circuit 50 converts the analog image signal output from the CDS/AGC circuit 48 into a digital image signal. The A/D conversion circuit 50 inputs the digital image signal after the A/D conversion to the processor device 16.

The processor device 16 includes a controller 52, a digital signal processor (DSP) 54, a noise reduction unit 56, a memory 58, an image processing unit 60, and a display control unit 62.

The controller 52 has a central processing unit (CPU), a read only memory (ROM) that stores a control program and setting data required for the control, and a random access memory (RAM) serving as a work memory that loads the control program. When the CPU executes the control program, the controller 52 controls respective units of the processor device 16.

The DSP 54 acquires the digital image signal from the endoscope 12, and performs various signal processing on the acquired image signal, for example, defect correction processing, offset processing, gain correction processing, linear matrix processing, gamma conversion processing, and demosaicing processing. The defect correction processing corrects a signal of a defect pixel of the image pick-up sensor 46. The offset processing removes a dark current component from the image signal after the defect correction processing and sets an accurate zero level. The gain correction processing adjusts the signal level by multiplying the image signal after the offset processing, by a specific gain.

The linear matrix processing increases the color reproducibility of the image signal after the gain correction processing. The gamma conversion processing adjusts the brightness and color saturation of the image signal after the linear matrix processing. By performing demosaicing processing (also referred to as isotropy processing) on the image signal after the gamma conversion processing, a signal of an insufficient color of each pixel is generated through interpolation. With the demosaicing processing, all pixels have signals of the respective colors of RGB.

The noise reduction unit 56 performs noise reduction processing by, for example, a moving average method or a median filter method, on the image signal after the demosaicing processing by the DSP 54 to reduce noise. The image signal after the noise reduction is stored in the memory 58.

The image processing unit 60 acquires the image signal from the memory 58, performs predetermined image processing on the acquired image signal, and generates a display image in which the observation object is captured. The content of image processing that is performed by the image processing unit 60 varies on an observation mode basis. The image processing unit 60 corresponds to an "image generation unit" of the present invention.

In the normal observation mode, the image processing unit 60 performs image processing, such as color conversion processing, chromatic emphasis processing, and structure emphasis processing, and generates a normal observation image. The color conversion processing is processing for performing color conversion on the image signal through 3×3 matrix processing, gradation transformation processing, and three-dimensional look-up table (LUT) processing. The chromatic emphasis processing is performed on the image signal after the color conversion processing. The structure emphasis processing is processing for emphasizing a specific tissue or structure included in an observation object, such as a blood vessel or a gland duct, and is performed on the image signal after the chromatic emphasis processing.

In the special observation mode, the image processing unit 60 performs the above-described various image processing for emphasizing the blood vessel and hence generates a special observation image. In the special observation mode, the emission light quantity of the V-LED 30a is large. Thus, in the special observation image, a surface layer blood vessel is emphasized.

In the suitable object observation mode, the image processing unit 60 performs the above-described various image processing for emphasizing the structure suitable for the diagnosis purpose and hence generates a suitable object observation image. In the suitable object observation mode, the illumination light with the light quantity ratio determined in accordance with the diagnosis purpose is used, and hence the structure suitable for the diagnosis purpose is emphasized in the suitable object observation image. For example, for the diagnosis purpose that focuses on a middle layer blood vessel, the blue light LB is used as illumination light, a surface layer blood vessel and so forth other than a middle layer blood vessel is plotted in a non-noticeable manner, and hence the middle layer blood vessel is enhanced.

The display control unit 62 causes the display unit 18 to display the display image generated by the image processing unit 60. Thus, the normal observation image is displayed in the normal observation mode, the special observation image is displayed in the special observation mode, and the suitable object observation image is displayed in the suitable object observation mode.

Next, light emission control in the suitable object observation mode is described. The processor device 16 further has a diagnosis purpose acquisition unit 64, a data transmission/reception unit 66, a light quantity ratio storage unit 68, and a light quantity ratio selection unit 70. The light quantity ratio storage unit 68 is composed of a recording medium, such as a hard disc drive (HDD) or a solid state drive (SSD).

The diagnosis purpose acquisition unit 64 acquires a diagnosis purpose from an endoscope information management system 72 connected to the diagnosis purpose acquisition unit 64 so as to communicate with each other through a network such as a local area network (LAN) via the data transmission/reception unit 66. The endoscope information management system 72 is a file server of a system such as a picture archiving and communication system (PACS) that files endoscope images. The endoscope information management system 72 has a data storage unit 74 that stores, as endoscope information management data, inspection information including a diagnosis purpose input from an input terminal (not illustrated), patient information, and so forth. The diagnosis purpose acquisition unit 64 receives the endoscope information management data from the data storage unit 74, and acquires the diagnosis purpose by extracting the diagnosis purpose from the endoscope information management data.

The light quantity ratio storage unit 68 stores correspondence between the diagnosis purpose and a plurality of light quantity ratios with different balances of respective emission light quantities of the V-LED 30a, the B-LED 30b, the G-LED 30c, and the R-LED 30d. Diagnosis purposes include a first diagnosis purpose including screening and close inspection, a second diagnosis purpose relating to the type of disease, and a third diagnosis purpose relating to the stage of disease. The first diagnosis purpose is not limited to the above-described screening and close inspection, and there are a variety of diagnosis purposes. For example, the first diagnosis purpose includes treatment, post-treatment surveillance, and so forth. The second diagnosis purpose includes, for example, Barrett's esophagus, large intestinal polyposis, and angiodysplasia. In addition to these, the second diagnosis purpose may be various diagnosis purposes, such as ulcerative colitis and esophagus squamous-cell carcinoma. The third diagnosis purpose is, for example, the remission period of ulcerative colitis and the active period of ulcerative colitis, which are determined in accordance with the type of disease.

As illustrated in FIG. 5, the light quantity ratio storage unit 68 has first to third light quantity ratio selection tables 68a to 68c. The first light quantity ratio selection table 68a stores a first diagnosis purpose and a light quantity ratio of the illumination light that is used for the first diagnosis purpose in an associated manner. For example, in the first light quantity ratio selection table 68a, large intestine screening is associated with a light quantity ratio R11 and a light quantity ratio R12; stomach screening is associated with a light quantity ratio R13; and large intestine close inspection is associated with a light quantity ratio R14. When the light quantity ratio is (the emission light quantity of the V-LED 30a):(the emission light quantity of the B-LED 30b):(the emission light quantity of the G-LED 30c):(the emission light quantity of the R-LED 30d), (that is, when V:B:G:R,) the light quantity ratio R11 is, for example, 1:0:0:0. The light quantity ratio R12 and the light quantity ratio R13 are the same light quantity ratio, and are each, for example, 0:1:0:0. The light quantity ratio R14 is, for example, the same as the light quantity ratio in the special observation mode.

The second light quantity ratio selection table 68b stores a second diagnosis purpose and a light quantity ratio of the illumination light that is used for the second diagnosis purpose in an associated manner. For example, in the second light quantity ratio selection table 68b, Barrett's esophagus is associated with a light quantity ratio R21 and a light quantity ratio R22; large intestinal polyposis is associated with a light quantity ratio R23; and angiodysplasia is associated with a light quantity ratio R24. The light quantity ratio R21 and the light quantity ratio R23 are, for example, 1:0:0:0. The light quantity ratio R22 and the light quantity ratio R24 are, for example, 0:1:0:0.

The third light quantity ratio selection table 68c stores a third diagnosis purpose and a light quantity ratio of the illumination light that is used for the third diagnosis purpose in an associated manner. For example, in the third light quantity ratio selection table 68c, the remission period of ulcerative colitis is associated with a light quantity ratio R31 and a light quantity ratio R32; and the active period of ulcerative colitis is associated with a light quantity ratio R33. The light quantity ratio R31 and the light quantity ratio R33 are, for example, 1:0:0:0. The light quantity ratio R32 is, for example, 0:1:0:0.

The correspondences stored in the first to third light quantity ratio selection tables 68a to 68c can be appropriately updated, for example, through an input operation with the instruction input part 19. Moreover, new correspondences can be added to the first to third light quantity ratio selection tables 68a to 68c.

The light quantity ratio selection unit 70 refers to the light quantity ratio storage unit 68 and selects the light quantity ratio that is used for the acquired diagnosis purpose. To be specific, the light quantity ratio selection unit 70 refers to the first light quantity ratio selection table 68a of the light quantity ratio storage unit 68 when acquiring the first diagnosis purpose; refers to the second light quantity ratio selection table 68b when acquiring the second diagnosis purpose; and refers to the third light quantity ratio selection table 68c when acquiring the third diagnosis purpose. That is, the light quantity ratio selection unit 70 selects the light quantity ratio in accordance with one diagnosis purpose of the first to third diagnosis purposes. Then, the light quantity ratio selection unit 70 inputs the selected light quantity ratio to the light source control unit 32.

Figure 6:
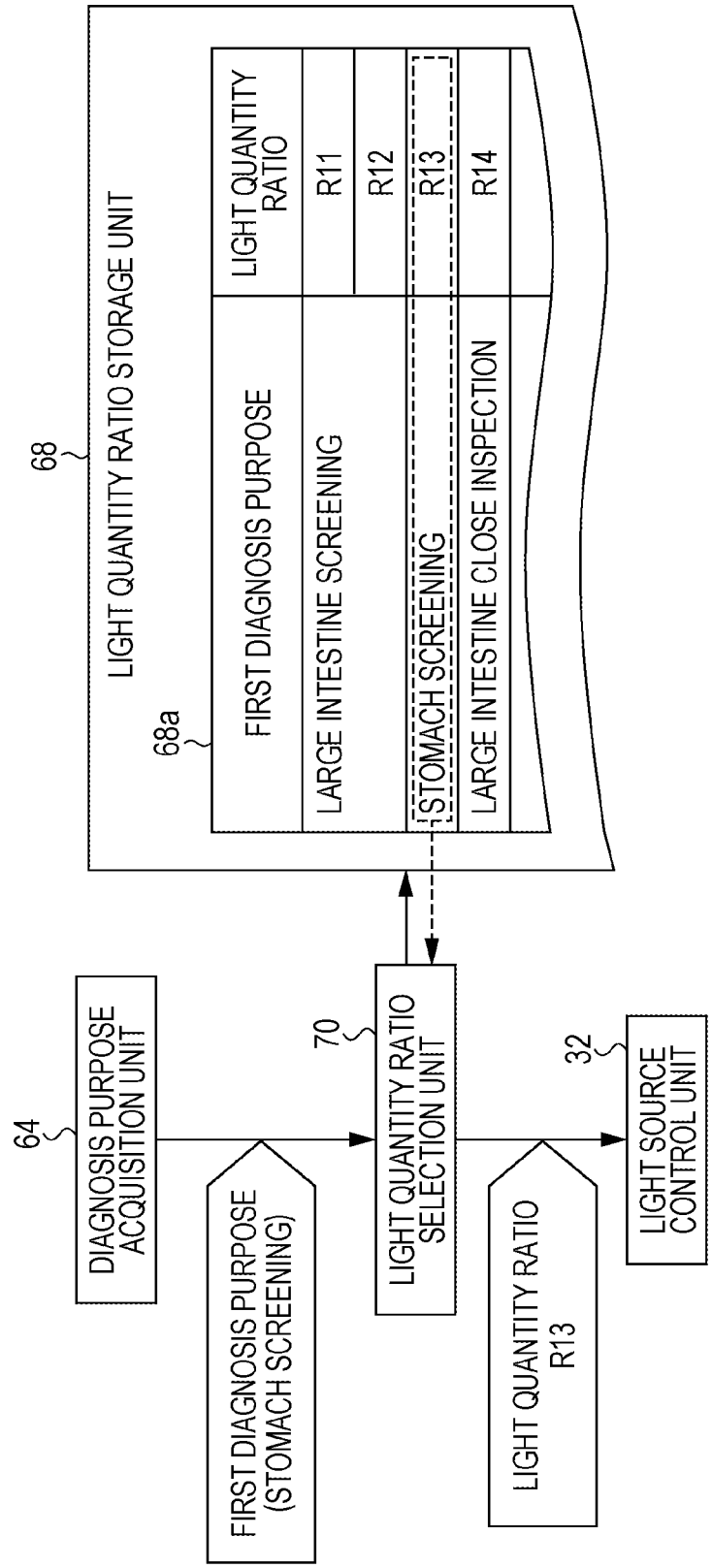
FIG. 6 is an illustration explaining a light quantity ratio selection unit.

For example, as illustrated in FIG. 6, when the acquired first diagnosis purpose is stomach screening, the light quantity ratio selection unit 70 refers to the first light quantity ratio selection table 68a, selects the light quantity ratio R13 associated with stomach screening, and inputs the light quantity ratio R13 to the light source control unit 32. In this embodiment, since the light quantity ratio R13 is 0:1:0:0, the light source control unit 32 turns ON only the B-LED 30b to emit the blue light LB as illumination light.

Figure 7A:
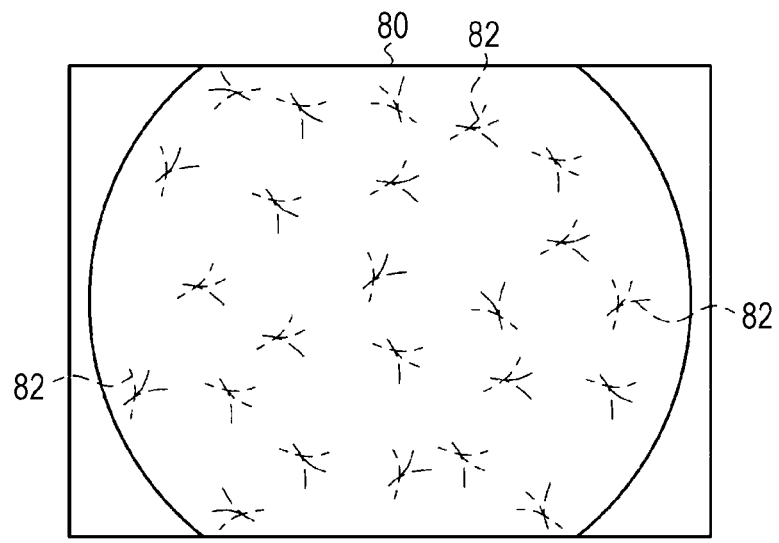
FIGS. 7A and 7B are illustrations explaining comparison between a normal observation image and a suitable observation image, FIG. 7A being a normal observation image, FIG. 7B being a suitable observation image.
Figure 7B:
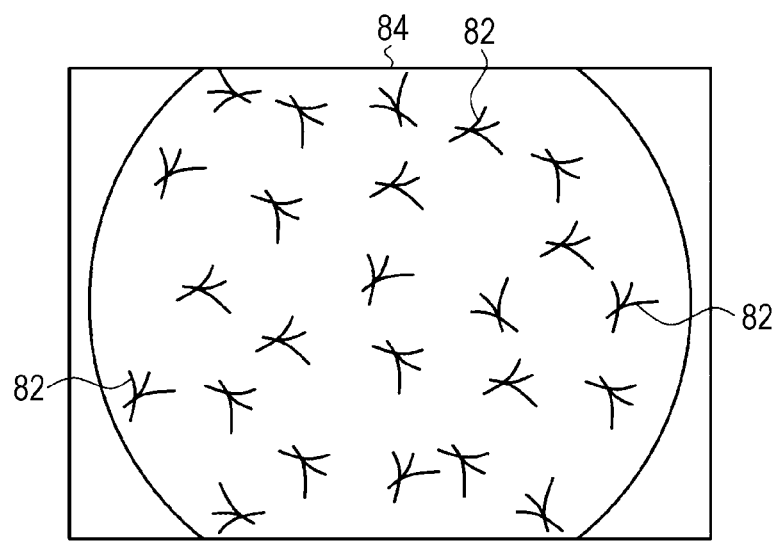

For normal screening, in many cases, a normal observation image is observed in the normal observation mode to check colors and so forth of an observation object. For stomach screening, it is requested to observe a middle layer blood vessel to check the presence of regular arrangement of collecting venules (RAC). As illustrated in FIG. 7A, in the normal observation mode, an observation object is captured with natural colors in a normal observation image 80 obtained by using the white light; however, the normal observation image 80 is not optimal for observing the RAC. In contrast, as illustrated in FIG. 7B, in the suitable object observation mode, a middle layer blood vessel 82 is, as compared with the normal observation image 80, displayed in a further emphasized manner in a suitable object observation image 84 obtained by using the illumination light with the light quantity ratio selected by the light quantity ratio selection unit 70, the illumination light which is the blue light LB. The RAC can be further assuredly observed.

In this embodiment, an example is described in which a single light quantity ratio is selected for a single diagnosis purpose. Thus, when a single diagnosis purpose is associated with a plurality of light quantity ratios in the light quantity ratio storage unit 68, the light quantity ratio selection unit 70 selects a single light quantity ratio designated through an operation with the instruction input part 19 from among the plurality of light quantity ratios. For example, when the first diagnosis purpose is large intestine screening and the light quantity ratio R11 is designated from among the light quantity ratio R11 and the light quantity ratio R12 by the instruction input part 19, the light quantity ratio selection unit 70 selects the light quantity ratio R11.

Figure 8:
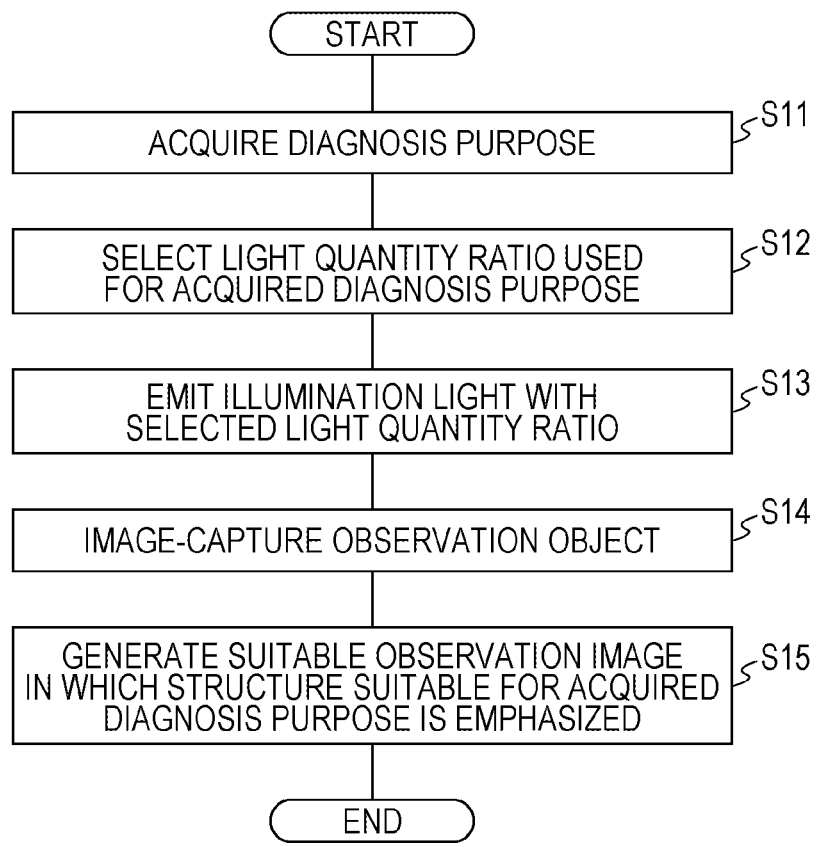
FIG. 8 is a flowchart explaining an operation in a suitable object observation mode of the endoscope system.

Next, an operation in the suitable object observation mode of the endoscope system 10 is described with reference to a flowchart in FIG. 8.

In the suitable object observation mode, the diagnosis purpose acquisition unit 64 acquires a diagnosis purpose from the data storage unit 74 of the endoscope information management system 72 through the network (S11). The diagnosis purpose acquisition unit 64 inputs the acquired diagnosis purpose to the light quantity ratio selection unit 70.

The light quantity ratio selection unit 70 refers to the light quantity ratio storage unit 68 and selects the light quantity ratio that is used for the acquired diagnosis purpose (S12). The light quantity ratio storage unit 68 stores correspondence between the diagnosis purpose and a plurality of light quantity ratios with different balances of respective emission light quantities of the V-LED 30a, the B-LED 30b, the G-LED 30c, and the R-LED 30d. To be specific, the light quantity ratio storage unit 68 has the first light quantity ratio selection table 68a storing the light quantity ratio of the illumination light that is used for the first diagnosis purpose; the second light quantity ratio selection table 68b storing the light quantity ratio of the illumination light that is used for the second diagnosis purpose; and the third light quantity ratio selection table 68c storing the light quantity ratio of the illumination light that is used for the third diagnosis purpose The light quantity ratio selection unit 70 selects the light quantity ratio from the first light quantity ratio selection table 68a when the acquired diagnosis purpose is the first diagnosis purpose; selects the light quantity ratio from the second light quantity ratio selection table 68b when the acquired diagnosis purpose is the second diagnosis purpose; and selects the light quantity ratio from the third light quantity ratio selection table 68c when the acquired diagnosis purpose is the third diagnosis purpose. Then, the light quantity ratio selection unit 70 inputs the selected light quantity ratio to the light source control unit 32. The light source control unit 32 controls the LEDs 30a to 30d to emit the illumination light with the light quantity ratio selected by the light quantity ratio selection unit 70 (S13).

The image pick-up sensor 46 image-captures the observation object illuminated with the illumination light (S14). The image processing unit 60 uses an image signal obtained by image-capturing and generates a suitable observation image in which a structure suitable for the diagnosis purpose is emphasized (S15). The display unit 18 displays the suitable observation image.

Since the diagnosis purpose acquisition unit 64 acquires a diagnosis purpose and the light quantity ratio selection unit 70 selects the light quantity ratio with which a structure suitable for the diagnosis purpose can be observed in this way, illumination light set to have the optimal balance of light source wavelengths in accordance with the diagnosis purpose can be emitted.

In the above-described first embodiment, the light quantity ratio selection unit 70 selects a single light quantity ratio for a single diagnosis purpose; however, for a diagnosis purpose that is requested to observe a plurality of structures, it is preferably select a plurality of light quantity ratios with which the structures can be observed. For example, for a diagnosis purpose that is requested for observing a surface layer blood vessel and a middle layer blood vessel, such as Barrett's esophagus, the light quantity ratio selection unit 70 refers to the second light quantity ratio selection tale 68b and selects the light quantity ratio R21 and the light quantity ratio R22 associated with Barrett's esophagus.

When the plurality of light quantity ratios are selected, the light source control unit 32 sequentially switches the light quantity ratios of the illumination light, and emits the illumination light. The image pick-up sensor 46 image-captures an observation object every time when the light source control unit 32 switches the light quantity ratio, and outputs the image signal. The image processing unit 60 generates a suitable object observation image every time when the image pick-up sensor 46 outputs the image signal.

Figure 9A:
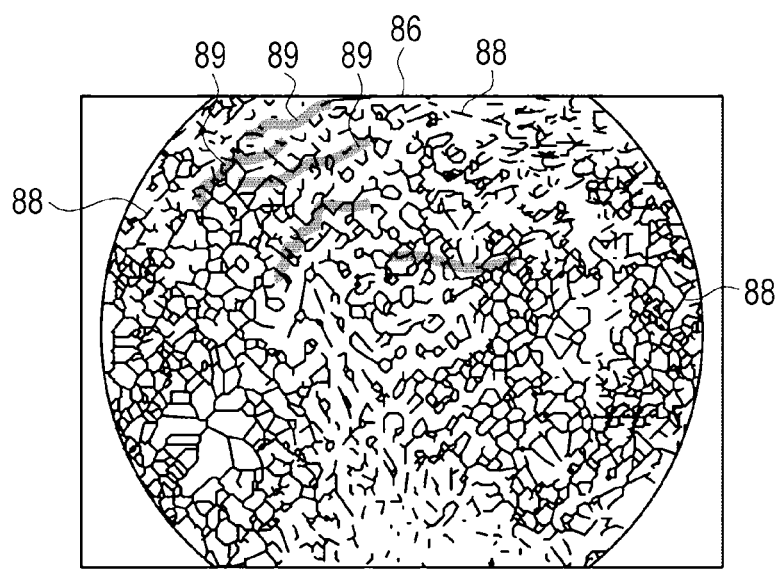
FIG. 9A is a suitable observation image obtained by using violet light and FIG. 9B is a suitable observation image obtained by using blue light.
Figure 9B:
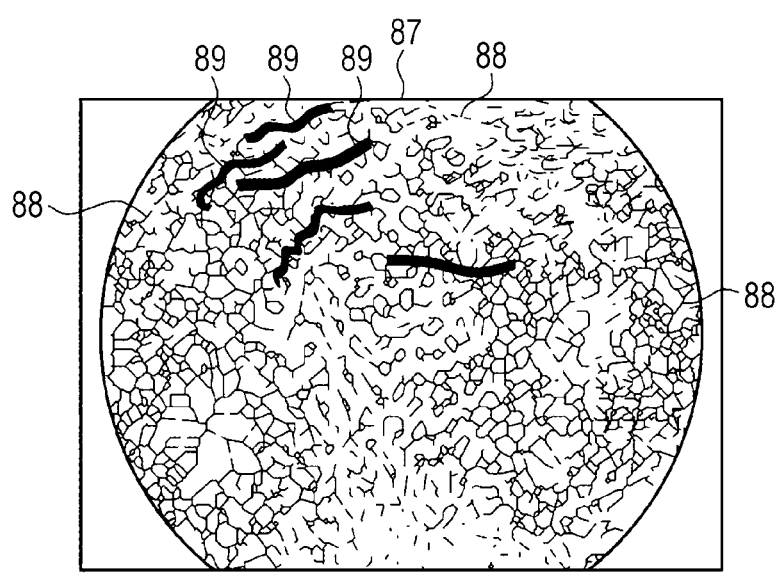

As illustrated in FIGS. 9A and 9B, for example, when the second diagnosis purpose acquired by the diagnosis purpose acquisition unit 64 is Barrett's esophagus, the image processing unit 60 sequentially generates two suitable object observation images 86 and 87. FIG. 9A is the suitable object observation image 86 obtained by using illumination light with the light quantity ratio R21, that is, the violet light LV. FIG. 9B is the suitable object observation image 87 obtained by using illumination light with the light quantity ratio R22, that is, the blue light LB. In the suitable object observation image 86, surface layer blood vessels 88 distributed in the entire screen are displayed in an emphasized manner whereas middle layer blood vessels 89 in an upper section of the screen are plotted in a not noticeable manner. In contrast, in the suitable object observation image 87, surface layer blood vessels 88 are plotted in a non-noticeable manner whereas middle layer blood vessels 89 are displayed in an emphasized manner. The display of the suitable object observation image 86 and the suitable object observation image 87 on the display unit 18 is switched through an operation with the instruction input part 19. In this case, the switching of display on the display unit 18 is not limited to switching through an operation with the instruction input part 19. For example, the display may be sequentially switched every time when a predetermined period elapses.

Figure 10:
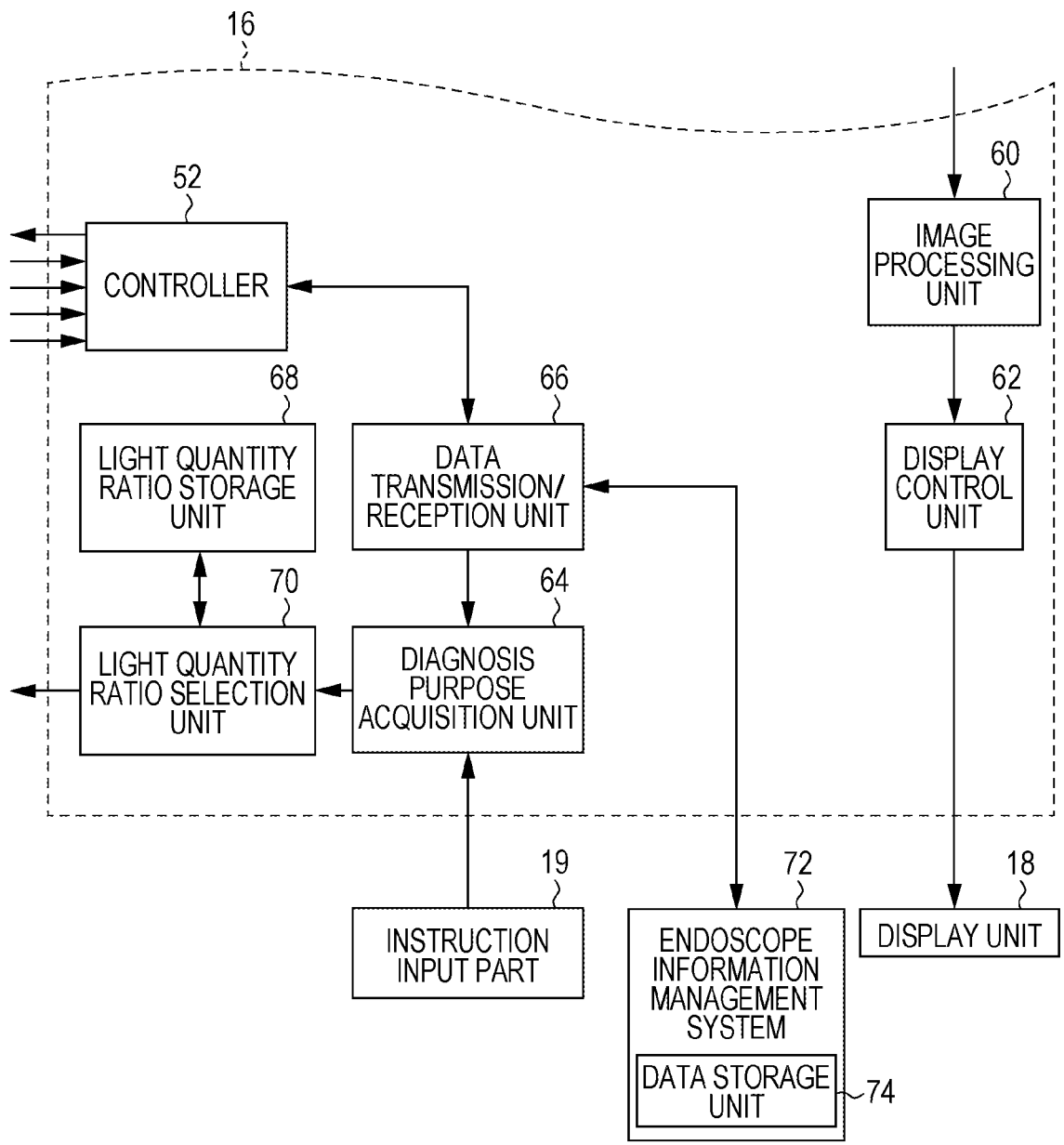
FIG. 10 is an illustration explaining acquisition of a diagnosis purpose from an instruction input part.

While the diagnosis purpose acquisition unit 64 acquires the diagnosis purpose from the endoscope information management system 72 through the network in the above-described first embodiment, as illustrated in FIG. 10, the diagnosis purpose acquisition unit 64 may acquire a diagnosis purpose input from the instruction input part 19 serving as a diagnosis purpose input unit, in addition to acquiring the diagnosis purpose from the endoscope information management system 72. In this case, the light quantity ratio selection unit 70 uses the diagnosis purpose input from the instruction input part 19 with higher priority and selects the light quantity ratio. Thus, during a diagnosis, the diagnosis purpose can be switched to a diagnosis purpose that is different from the diagnosis purpose acquired from the endoscope information management system 72, and the inspection can be continued.

Alternatively, the diagnosis purpose acquisition unit 64 may acquire the diagnosis purpose input from the instruction input part 19 instead of acquiring the diagnosis purpose from the endoscope information management system 72. In this case, the diagnosis purpose can be acquired even when the diagnosis purpose acquisition unit 64 is not connected to the endoscope information management system 72 through the network.

While a still image and/or a movie is stored in a storage (not illustrated), such as the HDD or the SSD when the image storage operation unit 26 is operated in the above-described first embodiment, the processor device 16 may be provided with an image storage unit 92 (see FIG. 11), and a suitable object observation image generated in the suitable object observation mode may be stored in association with at least one of the diagnosis purpose acquired by the diagnosis purpose acquisition unit 64 or the light quantity ratio selected by the light quantity ratio selection unit 70. A case where an image, a diagnosis purpose, and a light quantity ratio are stored in the image storage unit 92 is described below.

Figure 11:
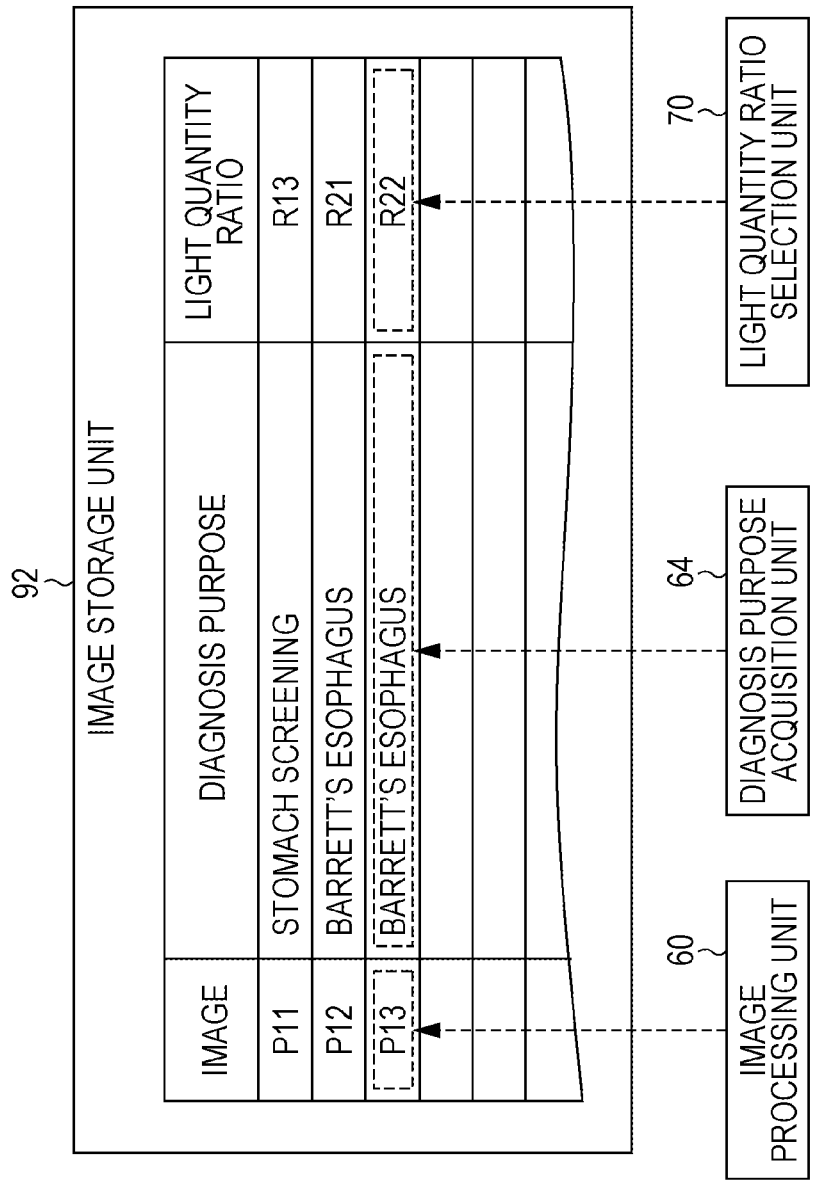
FIG. 11 is an illustration explaining an image storage unit.

For example, when the second diagnosis purpose acquired by the diagnosis purpose acquisition unit 64 is Barrett's esophagus, the light quantity ratio selection unit 70 selects the light quantity ratio R22 and the image processing unit 60 generates the suitable object observation image 87. When the image storage operating unit 26 is operated, as illustrated in FIG. 11, the image storage unit 92 stores the suitable object observation image 87 generated by the image processing unit 60 as an image "P13" for storage in a manner associated with the diagnosis purpose "Barrett's esophagus" acquired by the diagnosis purpose acquisition unit 64 and the light quantity ratio "R22" selected by the light quantity ratio selection unit 70.

The image, the diagnosis purpose, and the light quantity ratio stored in the image storage unit 92 can be displayed on the display unit 18. Accordingly, for a case of disease similar to the acquired diagnosis purpose, an image and a light quantity ratio can be displayed by search from the image storage unit 92 through an operation with the instruction input part 19. Moreover, an image and a diagnosis purpose can be searched by using the selected light quantity ratio.

Furthermore, when the image storage unit 92 is connected to the endoscope information management system 72 so as to mutually communicated with each other through the network, data stored in the image storage unit 92 is transmitted to and stored in the data storage unit 74, and hence data can be shared with an endoscope system different from the endoscope system 10.

In the above-described first embodiment, the diagnosis purpose acquisition unit 64 acquires one of the first to third diagnosis purposes. However, the diagnosis purpose acquisition unit 64 may acquire the first diagnosis purpose, the second diagnosis purpose, and the third diagnosis purpose. That is, the diagnosis purpose acquired by the diagnosis purpose acquisition unit 64 may include the first diagnosis purpose, the second diagnosis purpose, and the third diagnosis purpose.

In this case, the light quantity ratio selection unit 70 selects the light quantity ratio in accordance with a combination of the first to third diagnosis purposes acquired by the diagnosis purpose acquisition unit 64. An example combination of diagnosis purposes may be screening (the first diagnosis purpose) of the active period (the third diagnosis purpose) of ulcerative colitis (the second diagnosis purpose). In this example, the light quantity ratio selection unit 70 selects the light quantity ratio corresponding to large intestine screening from the first light quantity ratio selection table 68a, selects the light quantity ratio corresponding to ulcerative colitis from the second light quantity ratio selection table 68b, and selects the light quantity ratio corresponding to the active period of ulcerative colitis from the third light quantity ratio selection table 68c. Then, the light quantity ratio selection unit 70 inputs the selected light quantity ratios to the light source control unit 32. Thus, the light quantity ratios of the illumination light are sequentially switched. Accordingly, since the illumination light set to have the optimal balance of light source wavelengths in accordance with a plurality of diagnosis purposes, a diagnosis can be more specifically performed.

The diagnosis purpose acquisition unit 64 does not have to acquire the first diagnosis purpose, the second diagnosis purpose, and the third diagnosis purpose. Two or more diagnosis purposes from among the first to third diagnosis purposes may be acquired. That is, the diagnosis purpose acquired by the diagnosis purpose acquisition unit 64 may include two or more diagnosis purposes from among the first to third diagnosis purposes. In this case, the light quantity ratio selection unit 70 selects the light quantity ratios in accordance with a combination of two or more diagnosis purposes acquired by the diagnosis purpose acquisition unit 64.

Further, the diagnosis purpose acquisition unit 64 does not have to acquire the respective diagnosis purposes as described above, and may acquire a composite purpose in which a plurality of diagnosis purposes, such as the first diagnosis purpose and the second diagnosis purpose, are combined as the diagnosis purpose. In such a case, the light quantity ratio storage unit 68 is preferably provided with a light quantity ratio selection table for a composite purpose. The light quantity ratio selection table for a composite purpose stores a composite purpose and a light quantity ratio of the illumination light that is used for the composite purpose in an associated manner. The light quantity ratio of the illumination light that is used for the composite purpose is a light quantity ratio that is used for each diagnosis purpose constituting the composite purpose.

Second Embodiment

In the above-described first embodiment, a light quantity ratio with which a structure suitable for a diagnosis purpose can be observed is selected and hence the structure is emphasized. In contrast, in a second embodiment, an index value relating to a structure of an observation object is calculated, and the structure is emphasized by using the index value.

Figure 12:
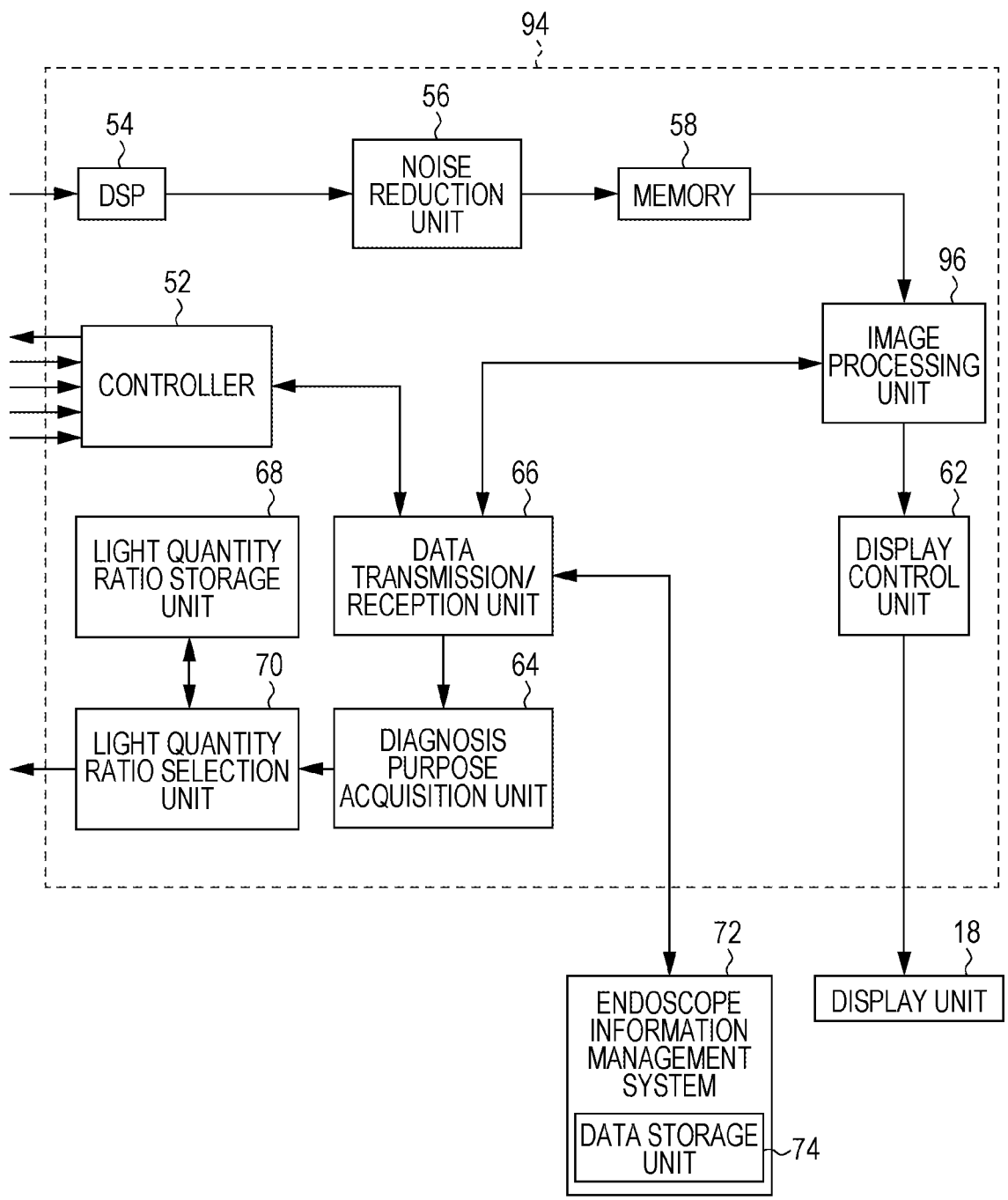
FIG. 12 is a block diagram illustrating a processor device according to a second embodiment.

As illustrated in FIG. 12, a processor device 94 includes an image processing unit 96 instead of the image processing unit 60. The image processing unit 96 acquires a diagnosis purpose from the diagnosis purpose acquisition unit 64.

Figure 13:
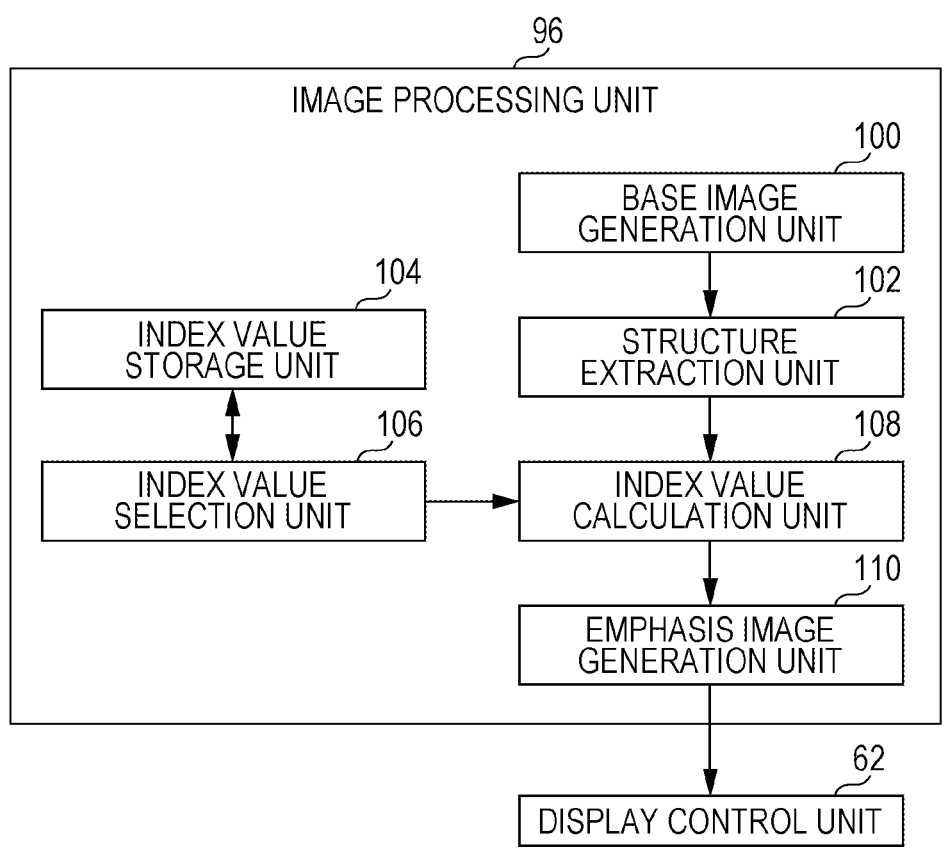
FIG. 13 is a block diagram explaining an image processing unit according to the second embodiment.

As illustrated in FIG. 13, the image processing unit 96 has a base image generation unit 100, a structure extraction unit 102, an index value storage unit 104, an index value selection unit 106, an index value calculation unit 108, and an emphasis image generation unit 110.

The base image generation unit 100 generates a base image, in which a structure of an observation object is expressed by using a difference in color, from an image signal acquired from the memory 58. The base image is expressed with a hue corresponding to the set light quantity ratio, and the hue is slightly different from that of a normal observation image. An example of the base image may be an image with a color balance that a white plate in an image obtained by imaging with the set light quantity ratio appears white; a gray image obtained by assigning an image signal to one of an R channel, a G channel, and a B channel of the display unit 18 (for example, when the light quantity of the green light LG is large in a light quantity ratio of illumination light; an image signal is assigned to the G channel); an image with a pseudo color obtained by changing the gradation balance of an image signal and assigning the image signal to one of the channels; and other images.

The structure extraction unit 102 generates a structure extraction image by extracting the structure of the observation object from the base image. For example, when the light source device 14 illuminates the observation object with illumination lights in different wavelength ranges, the structure extraction unit 102 extracts a blood vessel by taking a difference between images obtained by imaging the observation object illuminated with the respective illumination lights. To be specific, by taking a difference between an image obtained by imaging the observation object illuminated with the violet light LV and an image obtained by imaging the observation object illuminated with the blue light LB, a surface layer blood vessel or a blood vessel located at a shallower position than the position of the surface layer blood vessel can be extracted. In addition to or instead of extracting the blood vessel as described above, a structure of a gland duct may be extracted. The method of extracting a structure is not limited to the above-described method. In addition, while the structure extraction unit 102 extracts a blood vessel and a gland duct from the entirety of a base image in this embodiment, when a region of interest is designated by an operation with the instruction input part 19, a blood vessel and a gland duct may be extracted within only the designated region of interest.

The index value storage unit 104 stores correspondence between the diagnosis purpose and a plurality of index values relating to a structure of an observation object. The types of index values are, for example, the density of a blood vessel, the uniformity of the thickness of a blood vessel, the complexity of a blood vessel, and the uniformity of a surface structure. The types of index values are not limited to the above-described example.

The density of a blood vessel is the proportion of a blood vessel per unit area. The uniformity of the thickness of a blood vessel is an index value relating to a variation in the thickness of a blood vessel. The complexity of a blood vessel is an index value indicating the degree of complexity of the shape of a blood vessel. For example, the complexity of a blood vessel is a value calculated by combining the number of branch points of an extracted blood vessel (branch number), the degree of meandering of the blood vessel, the degree of curve of the extracted blood vessel (curvature), and so forth. The uniformity of a surface structure is an index value relating to a variation in the shape of a gland duct.

As illustrated in FIG. 14, the index value storage unit 104 has first to third index value selection tables 104a to 104c. The first index value selection table 104a stores a first diagnosis purpose and an index value that is used for the first diagnosis purpose in an associated manner. For example, in the first index value selection table 104a, large intestine screening is associated with the complexity of a surface layer blood vessel and the complexity of a middle layer blood vessel; stomach screening is associated with the complexity of a middle layer blood vessel and the uniformity of a surface structure; and large intestine close inspection is associated with the density of a surface layer blood vessel.

The second index value selection table 104b stores a second diagnosis purpose and an index value that is used for the second diagnosis purpose in an associated manner. For example, in the second index value selection table 104b, Barrett's esophagus is associated with the density of a surface layer blood vessel, the complexity of a surface layer blood vessel, the density of a middle layer blood vessel, and the complexity of a middle layer blood vessel; large intestinal polyposis is associated with the uniformity of the thickness of a middle layer blood vessel and the uniformity of a surface structure; and angiodysplasia is associated with the density of a middle layer blood vessel.

The third index value selection table 104c stores a third diagnosis purpose and an index value that is used for the third diagnosis purpose in an associated manner. For example, in the third index value selection table 104c, the remission period of ulcerative colitis is associated with the complexity of a surface layer blood vessel and the complexity of a middle layer blood vessel; and the active period of ulcerative colitis is associated with the complexity of a surface layer blood vessel.

The correspondences stored in the first to third index value selection tables 104a to 104c can be appropriately updated, for example, through an input operation with the instruction input part 19. Moreover, new correspondences can be added to the first to third index value selection tables 104a to 104c.

The index value selection unit 106 refers to the index value storage unit 104 and selects the index value that is used for the acquired diagnosis purpose. To be specific, the index value selection unit 106 refers to the first index value selection table 104a of the index value storage unit 104 when acquiring the first diagnosis purpose; refers to the second index value selection table 104b when acquiring the second diagnosis purpose; and refers to the third index value selection table 104c when acquiring the third diagnosis purpose. The index value selection unit 106 inputs the selected index value to the index value calculation unit 108.

Figure 15:
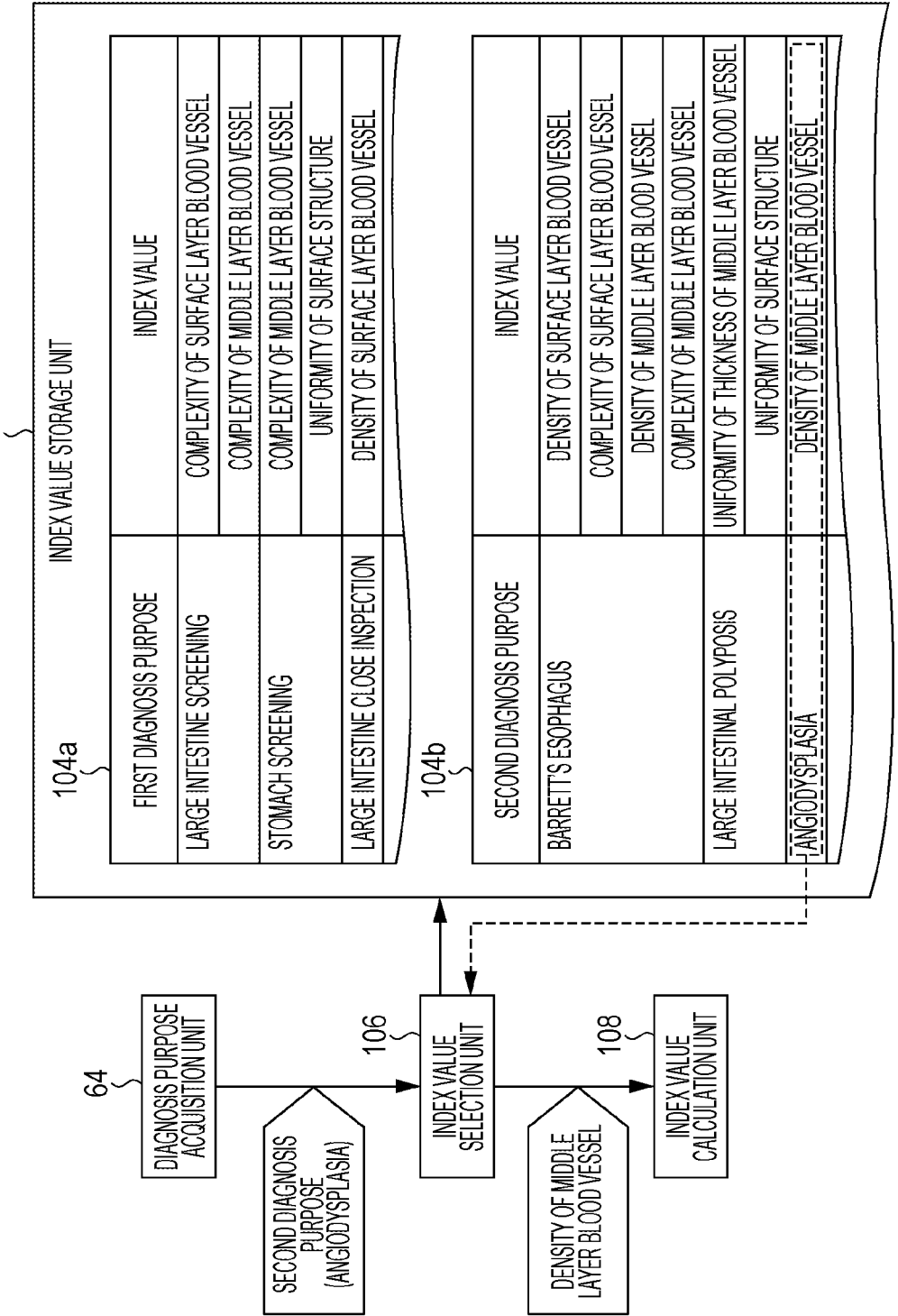
FIG. 15 is an illustration explaining an index value selection unit.

For example, as illustrated in FIG. 15, when the acquired second diagnosis purpose is angiodysplasia, the index value selection unit 106 refers to the second index value selection table 104b, selects the density of a middle layer blood vessel that is an index value associated with angiodysplasia, and inputs the density of a middle layer blood vessel to the index value calculation unit 108.

The index value calculation unit 108 calculates the selected index value from the structure extraction image. The index value calculation unit 108 calculates an index value for each pixel of the structure extraction image. For example, the index value calculation unit 108 calculates an index value of a single pixel by using data of pixels within a predetermined range including the pixels for which the index value is to be calculated (for example, a range of 99×99 pixels around the pixels for which the index value is to be calculated).

When a region of interest is set in part of the structure extraction image through an operation with the instruction input part 19, the index value calculation unit 108 calculates an index value within the set region of interest. When a region of interest is not set or when a region of interest is set for the entirety of the structure extraction image, the index value calculation unit 108 calculates an index value for the entirety of the structure extraction image.

The emphasis image generation unit 110 uses the generated base image and the calculated index value, and generates a suitable object observation image in which a structure suitable for the diagnosis purpose is further emphasized. The emphasis image generation unit 110 generates a suitable object observation image, for example, by performing overlap processing of overlaying information based on the index value, on the base image. The overlap processing may be coloring processing corresponding to the index value. In the suitable object observation image after the coloring processing, a region with an index value that is a certain value or larger is displayed with a pseudo color.

Figure 16:
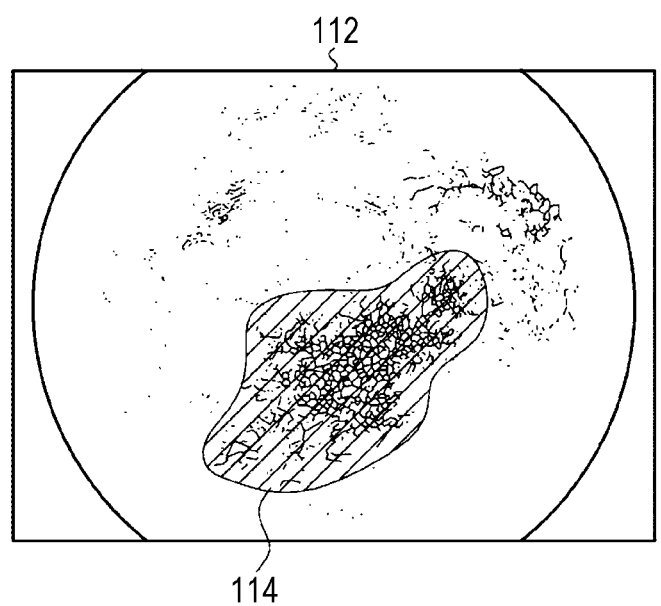
FIG. 16 illustrates a suitable observation image displayed in an emphasized manner by using an index value.

For example, in a structure emphasis image 112 illustrated in FIG. 16, a region 114 having a density of a middle layer blood vessel being a certain value or larger is displayed with a pseudo color. For example, a region with a large index value has a red-based color, and a region with a small index value has a blue-based color. In this case, information indicating the value of the index value may be overlaid on the base image. Thus, a structure suitable for the diagnosis purpose can be further emphasized.

The processor device 94 may be provided with an image storage unit 116 (see FIG. 17), and a suitable object observation image generated in the suitable object observation mode may be stored in association with the diagnosis purpose acquired by the diagnosis purpose acquisition unit 64, the light quantity ratio selected by the light quantity ratio selection unit 70, and the index value calculated by the index value calculation unit 108.

Figure 17:
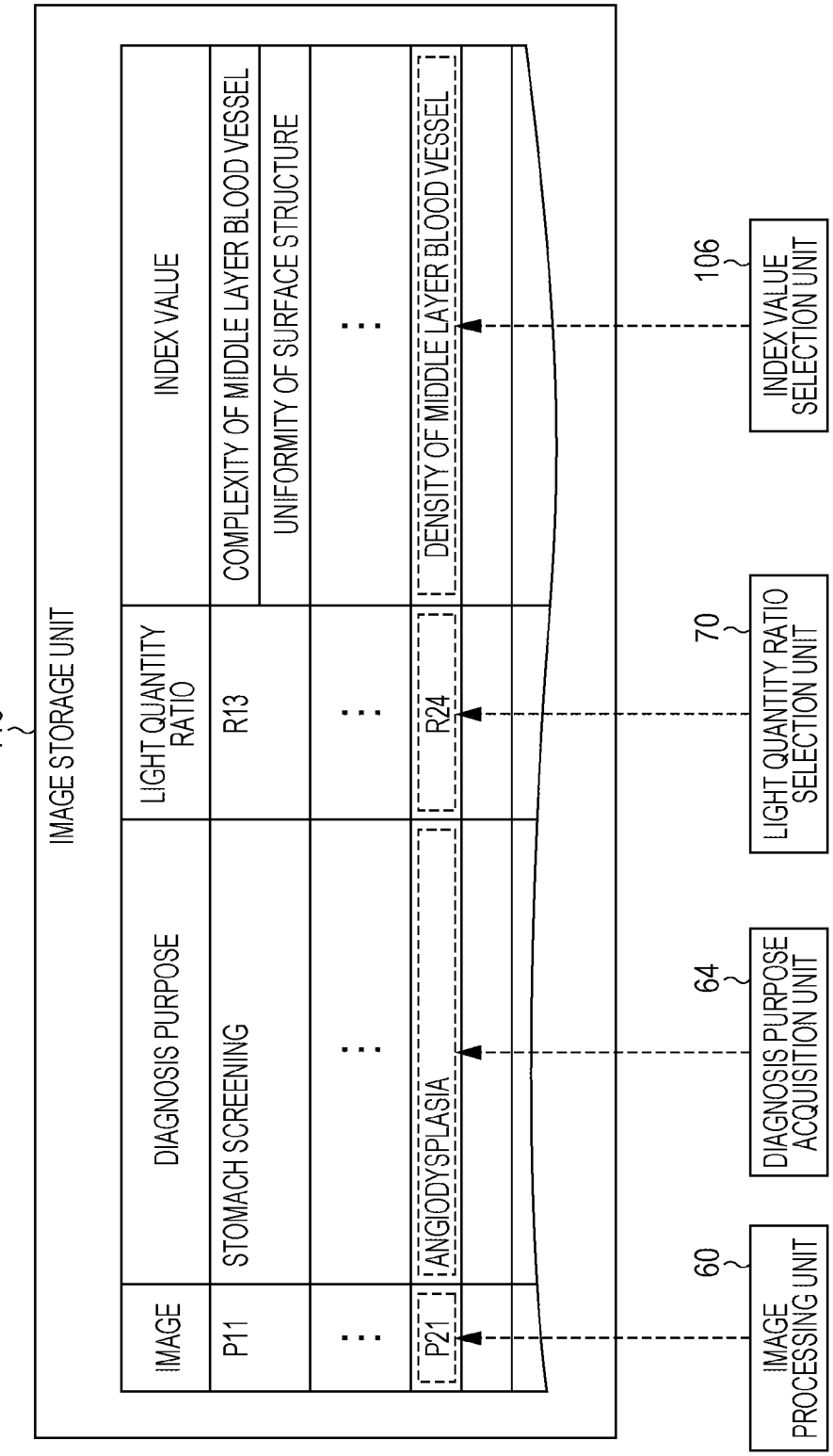
FIG. 17 is an illustration explaining an image storage unit according to the second embodiment.

For example, when the second diagnosis purpose acquired by the diagnosis purpose acquisition unit 64 is angiodysplasia, the light quantity ratio selection unit 70 selects the light quantity ratio R22 and the index value selection unit 106 selects the density of a middle layer blood vessel. The index value calculation unit 108 calculates the density of a middle layer blood vessel from the extraction image generated by the structure extraction unit 102. The emphasis image generation unit 110 uses the base image generated by the base image generation unit 100 and the calculated density of a middle layer blood vessel, and generates a suitable object observation image. When the image storage operating unit 26 is operated, as illustrated in FIG. 17, the image storage unit 116 stores the suitable object observation image generated by the emphasis image generation unit 110 as an image P21 for storage, in a manner associated with the diagnosis purpose "angiodysplasia" acquired by the diagnosis purpose acquisition unit 64, the light quantity ratio "R24" selected by the light quantity ratio selection unit 70, and "the density of a middle layer blood vessel" that is the index value selected by the index value selection unit 106.

Third Embodiment

Figure 18:
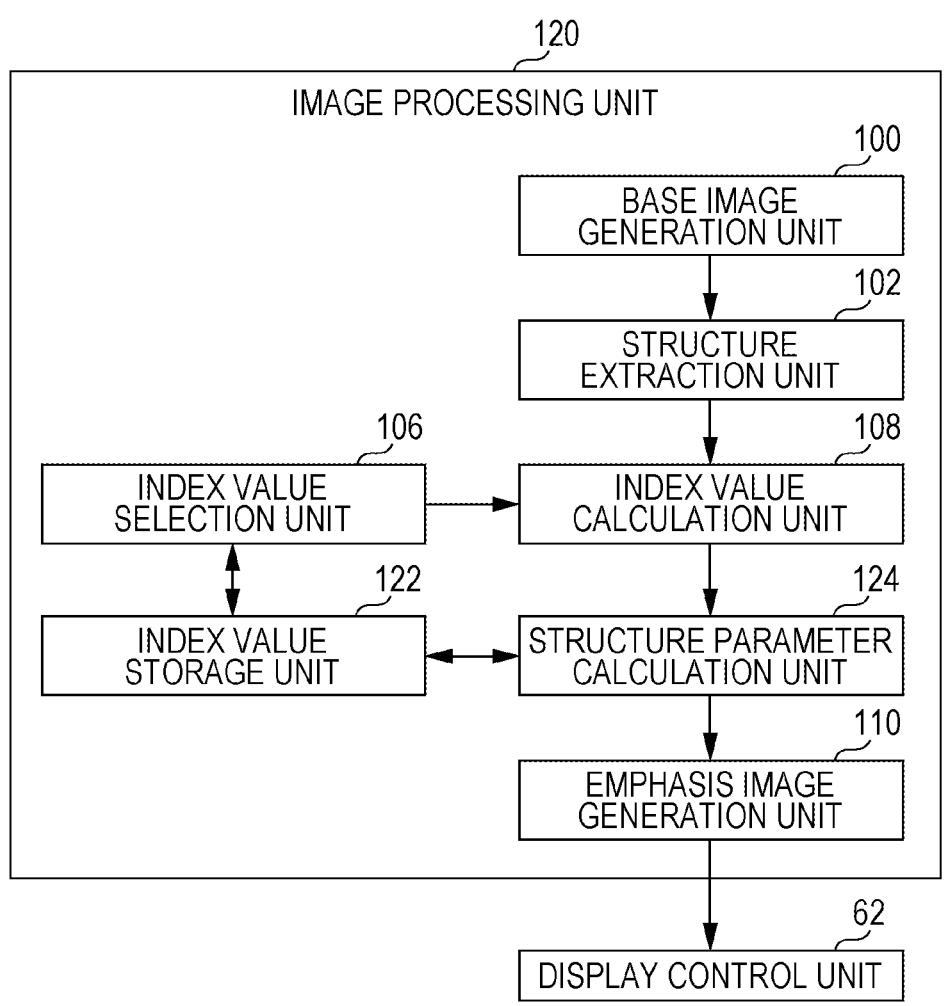
FIG. 18 is a block diagram explaining an image processing unit according to a third embodiment.

In the above-described second embodiment, the emphasis image generation unit 110 provides the emphasis display using the index value. In contrast, in a third embodiment, a structure parameter is calculated by using a plurality of index values, and emphasis display is provided by using the structure parameter. In the third embodiment, an image processing unit 120 (see FIG. 18) is included instead of the image processing unit 96 of the second embodiment.

The image processing unit 120 has an index value storage unit 122 instead of the index value storage unit 104 of the second embodiment. Moreover, the image processing unit 120 has a structure parameter calculation unit 124 in addition to the respective units of the image processing unit 96 of the second embodiment.

The index value storage unit 122 further stores, in addition to the index value and the diagnosis purpose, a weighting coefficient that is used by a structure parameter calculation unit (described later) in an associated manner.

As illustrated in FIG. 19, the index value storage unit 122 has first to third index value selection tables 122a to 122c. Regarding the first to third index value selection tables 122a to 122c, the relationship between the diagnosis purpose and the index value is the same as that of the index value storage unit 104 of the second embodiment, and hence the description thereof is omitted. The relationship with the weighting coefficient (hereinafter, referred to as coefficient) is described below.

The first index value selection table 122a stores a first diagnosis purpose, an index value that is used for the first diagnosis purpose, and a coefficient in an associated manner. For example, regarding large intestine screening, the coefficient for the complexity of a surface layer blood vessel is 0.5, and the coefficient for the complexity of a middle layer blood vessel is 1. Regarding stomach screening, the coefficient for the complexity of a middle layer blood vessel is 1, and the coefficient for the uniformity of a surface structure is 1. Regarding large intestine close inspection, the coefficient for the density of a surface layer blood vessel is 1.

The second index value selection table 122b stores a second diagnosis purpose, an index value that is used for the second diagnosis purpose, and a coefficient in an associated manner. For example, regarding Barrett's esophagus, the coefficient for the density of a surface layer blood vessel, the coefficient for the complexity of a surface layer blood vessel, the coefficient for the density of a middle layer blood vessel, and the coefficient for the complexity of a middle layer blood vessel each are 1. Regarding large intestinal polyposis, the coefficient for the uniformity of the thickness of a middle layer blood vessel is 1, and the coefficient for the uniformity of a surface structure is 0.5. Regarding angiodysplasia, the coefficient for the density of a middle layer blood vessel is 1.

The third index value selection table 122c stores a third diagnosis purpose, an index value that is used for the third diagnosis purpose, and a coefficient in an associated manner. For example, regarding the remission period of ulcerative colitis, the coefficient for the complexity of a surface layer blood vessel and the coefficient for the complexity of a middle layer blood vessel each are 1. Regarding the active period of ulcerative colitis, the coefficient for the complexity of a surface layer blood vessel is 1.

The correspondences stored in the first to third index value selection tables 122a to 122c can be appropriately updated, for example, through an input operation with the instruction input part 19. Moreover, new correspondences can be added to the first to third index value selection tables 122a to 122c.

In the third embodiment, the diagnosis purpose acquisition unit 64 acquires one of the first to third diagnosis purposes. However, it is not limited thereto, and the diagnosis purpose acquisition unit 64 may acquire a composite purpose. To prepare for such a case, the index value storage unit 122 may be provided with an index value selection table for a composite purpose. The index value selection table for a composite purpose stores a composite purpose, index values that are used for the composite purpose, and a coefficient in an associated manner. The index values that are used for the composite purpose are index values that are used for respective diagnosis purposes constituting the composite purpose. The coefficient stored in the index value selection table for a composite purpose is set, for example, to a larger value for index values that overlap one another by a larger number among the index values that are used for the respective diagnosis purposes constituting the composite purpose.

The structure parameter calculation unit 124 calculates a structure parameter by using the index value calculated by the index value calculation unit 108. To be specific, the structure parameter calculation unit 124 calculates a structure parameter by weighting a plurality of index values with a coefficient (weighting coefficient) determined in accordance with the diagnosis purpose and arithmetically operating the index values. The structure parameter calculation unit 124, when calculating the structure parameter, refers to the index value storage unit 122 and uses the coefficient associated with the index value calculated by the index value calculation unit 108.

The structure parameter is a numerical value that is calculated by using index values in such a way of imitating the viewpoint of a doctor who carries out a diagnosis with regard to the entirety of the index values. For example, the structure parameter is calculated through arithmetic operation such as addition of index values having mutually different dimensions (units), and hence the structure parameter has no physical meaning; however, the structure parameter functions as an index of a diagnosis. That is, the structure parameter differs from the index value in that the structure parameter has no physical meaning.

For example, when the second diagnosis purpose acquired by the diagnosis purpose acquisition unit 64 is Barrett's esophagus, the structure parameter calculation unit 124 calculates a structure parameter by multiplying each of the density of a surface layer blood vessel, the complexity of a surface layer blood vessel, the density of a middle layer blood vessel, and the complexity of a middle layer blood vessel by 1 and adding these values. While the structure parameter calculation unit 124 calculates a single structure parameter by using a plurality of index values in this embodiment, it is not limited thereto, and the structure parameter calculation unit 124 may calculate two or more structure parameters. The structure parameter may be calculated by any method. For example, without being limited to the calculation of the structure parameter using the weighted sum of the plurality of index values as described above, a structure parameter may be calculated through arithmetic operation involving mixture of at least two of addition, subtraction, multiplication, and division, or a structure parameter may be calculated by using any of other functions.

The emphasis image generation unit 110 uses the generated base image and the calculated structure parameter, and generates a suitable object observation image. The emphasis image generation unit 110 generates a suitable object observation image, for example, by performing overlap processing of overlaying information based on the structure parameter, on the base image.

Figure 20:
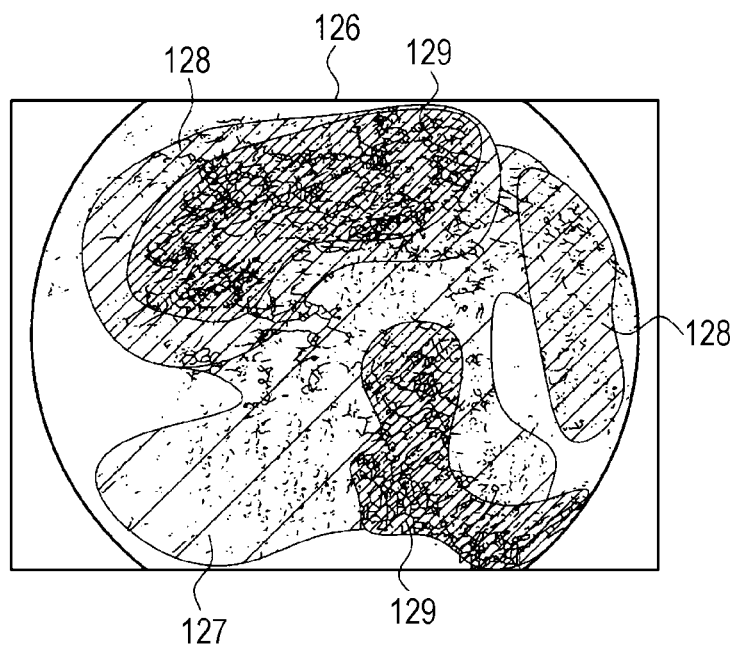
FIG. 20 illustrates a suitable observation image displayed in an emphasized manner by using a structure parameter.

For example, in a suitable object observation image 126 illustrated in FIG. 20, regions 127 to 129 are displayed with different colors in accordance with the structure parameters. For example, the region 127 among the regions 127 to 129 has the smallest structure parameter and hence has a blue-based color. The region 128 has a larger structure parameter than the region 127 and hence has a yellow-based color. The region 129 has a larger structure parameter than the region 128 and hence has a red-based color. In this case, information indicating the value of the structure parameter may be overlaid on the base image. Thus, a structure suitable for the diagnosis purpose can be further emphasized.

Fourth Embodiment

Figure 21:
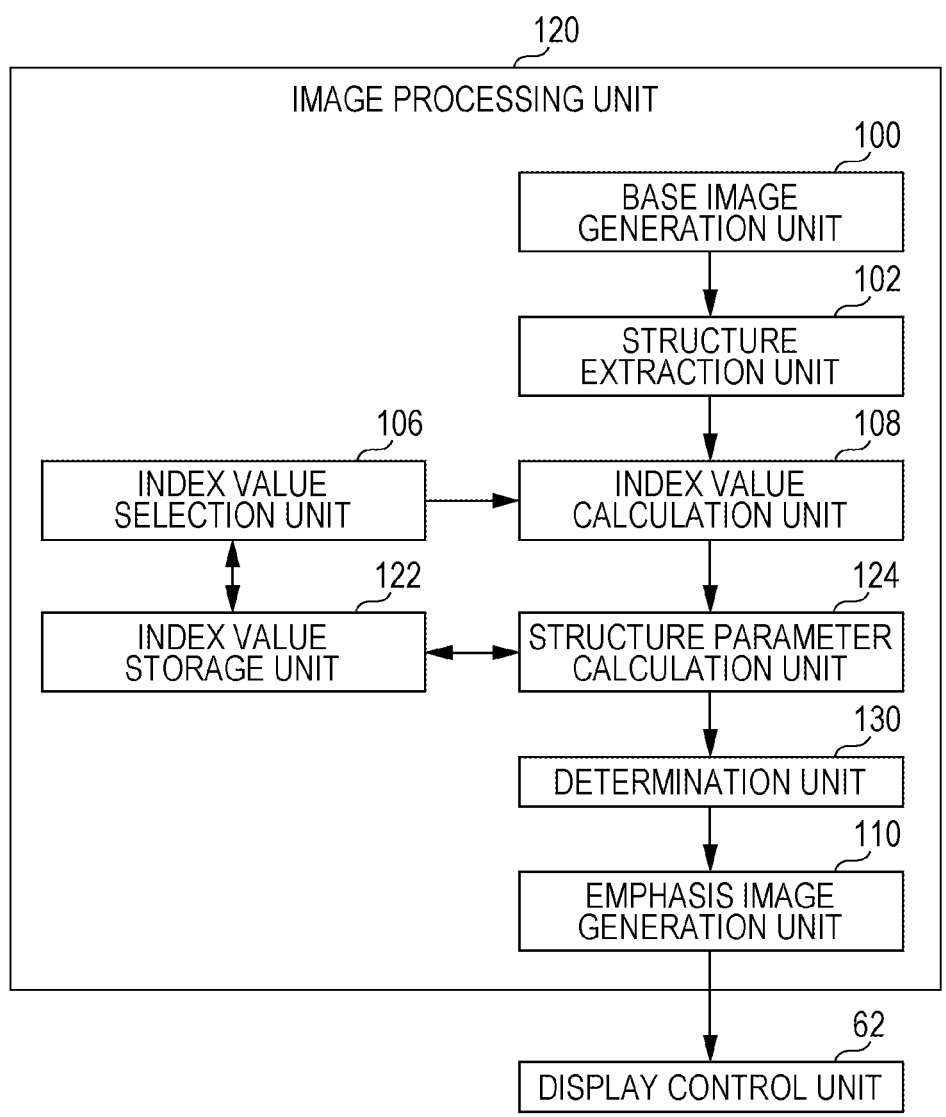
FIG. 21 is a block diagram explaining an image processing unit according to a fourth embodiment.

In the above-described third embodiment, the emphasis image generation unit 110 provides the emphasis display using the structure parameter. In contrast, in a fourth embodiment, the state of a mucous membrane of an observation object is determined by using a structure parameter, and emphasis display is provided by using the determination result. The image processing unit 120 in this case further has a determination unit 130 illustrated in FIG. 21.

The determination unit 130 determines the state of the mucous membrane of the observation object by using the structure parameter calculated by the structure parameter calculation unit 124. "The state of a mucous membrane" of an observation object is a comprehensive status of the entirety of a mucous membrane including a blood vessel and a gland duct, and is, for example, "normal", "adenoma (suspected adenoma)", "cancer (suspected cancer)", or other status. Thus, the determination unit 130 determines the state of the mucous membrane as being in one of three types of states of normal, adenoma, and cancer.

For example, it is assumed that a coefficient that is used for calculating a structure parameter is set to a balance that can determine one of the three types of states of normal, adenoma, and cancer. In this case, the determination unit 130 determines the state of a mucous membrane by comparing a numerical value of the structure parameter and a threshold value. To be specific, when the structure parameter is equal to or smaller than a first threshold value, the determination unit 130 determines that the state of the mucous membrane of the observation object is "normal". When the structure parameter is larger than the first threshold value and equal to or smaller than a second threshold value, the determination unit 130 determines that the state of the mucous membrane of the observation object is "adenoma". When the structure parameter is larger than the second threshold value, the determination unit 130 determines that the state of the mucous membrane of the observation object is "cancer".

The emphasis image generation unit 110 uses the generated base image and the determination result of the determination unit 130, and generates a suitable object observation image. The emphasis image generation unit 110 generates a suitable object observation image, for example, by performing overlap processing of overlaying information based on the determination result, on the base image.

Figure 22:
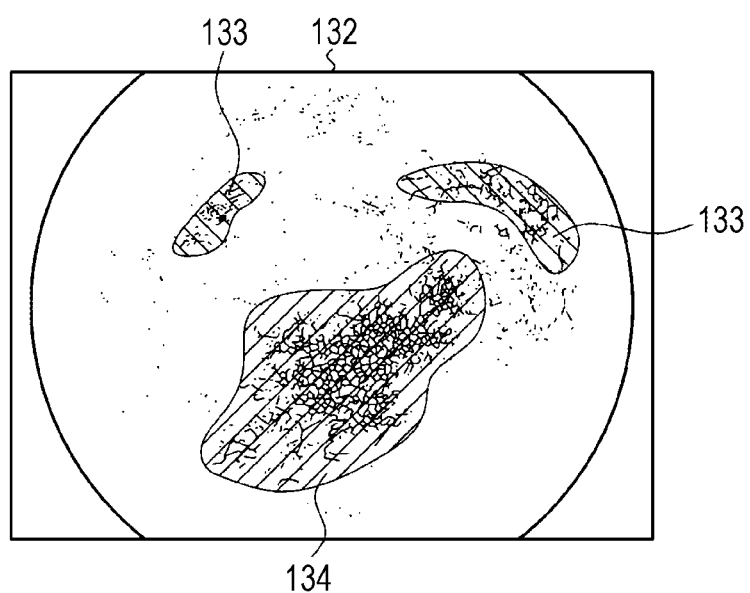
FIG. 22 illustrates a suitable observation image displayed in an emphasized manner by using a determination result.

For example, in a suitable object observation image 132 illustrated in FIG. 22, a region 133 is a region that is determined as "adenoma". A region 134 is a region that is determined as "cancer". The region 133 and the region 134 are displayed with different colors. For example, the region 133 has a yellow-based color, and the region 134 has a red-based color. The region determined as "normal" is not colored in this embodiment; however, the region may be colored with, for example, a blue-based color. Information indicating the determination result may be displayed for the base image. By determining the state of a mucous membrane of an observation object using a structure parameter and displaying the determination result in this way, a diagnosis can be further directly assisted.

REFERENCE SIGNS LIST 10 endoscope system
12 endoscope
12a insertion section
12b operation section
14 light source device
16 processor device
18 display unit
21 instruction input part
21 distal end portion
22 bending portion
23 flexible pipe portion
25 angle knob
26 image storage operating unit
27 mode switching unit
28 zoom operating unit
30 light source
30a V-LED
30b B-LED
30c G-LED
30d R-LED
30e optical filter
32 light source control unit
34 light guide
36 illumination optical system
38 image pick-up optical system
40 illumination lens
42 objective lens
44 zoom lens
46 image pick-up sensor
48 CDS/AGC circuit
50 A/D conversion circuit
52 controller
54 DSP
56 noise reduction unit
58 memory
60 image processing unit
62 display control unit
64 diagnosis purpose acquisition unit
66 data transmission/reception unit
68 light quantity ratio storage unit
68a first light quantity ratio selection table
68b second light quantity ratio selection table
68c third light quantity ratio selection table
70 light quantity ratio selection unit
72 endoscope information management system
74 data storage unit
80 normal observation image
82 middle layer blood vessel
84 suitable object observation image
86 suitable object observation image
87 suitable object observation image
88 surface layer blood vessel
89 middle layer blood vessel
92 image storage unit
94 processor device
96 image processing unit
100 base image generation unit
102 structure extraction unit
104 index value storage unit
104a first index value selection table
104b second index value selection table
104c third index value selection table
106 index value selection unit
108 index value calculation unit
110 emphasis image generation unit
112 suitable object observation image
114 region
116 image storage unit
120 image processing unit
122 index value storage unit
122a first index value selection table
122b second index value selection table
122c third index value selection table
124 structure parameter calculation unit
126 suitable object observation image
127 region
128 region
129 region
130 determination unit
132 suitable object observation image
133 region
134 region

What is claimed is:
1. An endoscope system comprising:
a diagnosis purpose acquisition unit that acquires a diagnosis purpose;
a plurality of light sources with different light emission wavelengths;
a light quantity ratio storage unit that stores correspondence between the diagnosis purpose and a plurality of light quantity ratios with different balances of respective emission light quantities of the plurality of light sources;
a light quantity ratio selection unit that refers to the light quantity ratio storage unit and selects a light quantity ratio that is used for the acquired diagnosis purpose;
a light source control unit that controls the plurality of light sources to emit illumination light with the selected light quantity ratio;
an image generation unit that generates an image by using an image signal that is obtained by an endoscope image-capturing an observation object illuminated with the illumination light;
an image storage unit that stores the image in association with at least one of the acquired diagnosis purpose or the selected light quantity ratio;
an index value storage unit that stores correspondence between the diagnosis purpose and a plurality of index values relating to a structure of the observation object;
an index value selection unit that selects an index value that is used for the acquired diagnosis purpose, from among the index values stored in the index value storage unit; and
an index value calculation unit that uses the image and calculates the selected index value;
wherein the image generation unit uses the calculated index value and generates, as the image, an image in which the structure is displayed in an emphasized manner; and
a structure parameter calculation unit that calculates a structure parameter of the structure by weighting a plurality of the index values with a weighting coefficient determined in accordance with the diagnosis purpose and arithmetically operating the index values.

2. The endoscope system according to claim 1,
wherein the diagnosis purpose includes a first diagnosis purpose including screening and close inspection, a second diagnosis purpose relating to a type of disease, and a third diagnosis purpose relating to a stage of disease, and
wherein the light quantity ratio selection unit selects the light quantity ratio in accordance with a combination of the first to third diagnosis purposes.

3. The endoscope system according to claim 1,
wherein the diagnosis purpose includes a first diagnosis purpose including screening and close inspection, a second diagnosis purpose relating to a type of disease, and a third diagnosis purpose relating to a stage of disease, and
wherein the light quantity ratio selection unit selects the light quantity ratio in accordance with one diagnosis purpose of the first to third diagnosis purposes.

4. The endoscope system according to claim 1, wherein the image generation unit uses the calculated structure parameter and generates, as the image, an image in which the structure is displayed in an emphasized manner.

5. The endoscope system according to claim 1, wherein the image storage unit stores the image further in association with the calculated structure parameter.

6. The endoscope system according to claim 1,
wherein the endoscope system is connected to an endoscope information management system having a data storage unit that stores endoscope information management data including the diagnosis purpose so as to mutually communicate with each other through a network, and
wherein the diagnosis purpose acquisition unit receives the endoscope information management data through the network, and acquires the diagnosis purpose by extracting the diagnosis purpose from the received endoscope information management data.

7. The endoscope system according to claim 2,
wherein the endoscope system is connected to an endoscope information management system having a data storage unit that stores endoscope information management data including the diagnosis purpose so as to mutually communicate with each other through a network, and
wherein the diagnosis purpose acquisition unit receives the endoscope information management data through the network, and acquires the diagnosis purpose by extracting the diagnosis purpose from the received endoscope information management data.

8. The endoscope system according to claim 3,
wherein the endoscope system is connected to an endoscope information management system having a data storage unit that stores endoscope information management data including the diagnosis purpose so as to mutually communicate with each other through a network, and
wherein the diagnosis purpose acquisition unit receives the endoscope information management data through the network, and acquires the diagnosis purpose by extracting the diagnosis purpose from the received endoscope information management data.

9. The endoscope system according to claim 4,
wherein the endoscope system is connected to an endoscope information management system having a data storage unit that stores endoscope information management data including the diagnosis purpose so as to mutually communicate with each other through a network, and
wherein the diagnosis purpose acquisition unit receives the endoscope information management data through the network, and acquires the diagnosis purpose by extracting the diagnosis purpose from the received endoscope information management data.

10. The endoscope system according to claim 5,
wherein the endoscope system is connected to an endoscope information management system having a data storage unit that stores endoscope information management data including the diagnosis purpose so as to mutually communicate with each other through a network, and
wherein the diagnosis purpose acquisition unit receives the endoscope information management data through the network, and acquires the diagnosis purpose by extracting the diagnosis purpose from the received endoscope information management data.

11. The endoscope system according to any one of claim 1, further comprising:
a diagnosis purpose input unit that inputs the diagnosis purpose,
wherein the diagnosis purpose acquisition unit acquires the diagnosis purpose input by the diagnosis purpose input unit.

12. The endoscope system according to any one of claim 2, further comprising:
a diagnosis purpose input unit that inputs the diagnosis purpose,
wherein the diagnosis purpose acquisition unit acquires the diagnosis purpose input by the diagnosis purpose input unit.

13. The endoscope system according to any one of claim 3, further comprising:
a diagnosis purpose input unit that inputs the diagnosis purpose,
wherein the diagnosis purpose acquisition unit acquires the diagnosis purpose input by the diagnosis purpose input unit.

14. The endoscope system according to any one of claim 4, further comprising:
a diagnosis purpose input unit that inputs the diagnosis purpose,
wherein the diagnosis purpose acquisition unit acquires the diagnosis purpose input by the diagnosis purpose input unit.

15. The endoscope system according to any one of claim 5, further comprising:
a diagnosis purpose input unit that inputs the diagnosis purpose,
wherein the diagnosis purpose acquisition unit acquires the diagnosis purpose input by the diagnosis purpose input unit.

16. An endoscope system comprising:
a diagnosis purpose acquisition unit that acquires a diagnosis purpose;
a plurality of light sources with different light emission wavelengths;
a light quantity ratio storage unit that stores correspondence between the diagnosis purpose and a plurality of light quantity ratios with different balances of respective emission light quantities of the plurality of light sources;

a light quantity ratio selection unit that refers to the light quantity ratio storage unit and selects a light quantity ratio that is used for the acquired diagnosis purpose;
a light source control unit that controls the plurality of light sources to emit illumination light with the selected light quantity ratio;
an image generation unit that generates an image by using an image signal that is obtained by an endoscope image-capturing an observation object illuminated with the illumination light;
an image storage unit that stores the image in association with at least one of the acquired diagnosis purpose or the selected light quantity ratio;
an index value storage unit that stores correspondence between the diagnosis purpose and a plurality of index values relating to a structure of the observation object;
an index value selection unit that selects an index value that is used for the acquired diagnosis purpose, from among the index values stored in the index value storage unit; and
an index value calculation unit that uses the image and calculates the selected index value;
wherein the image generation unit uses the calculated index value and generates, as the image, an image in which the structure is displayed in an emphasized manner; and
a structure parameter calculation unit that calculates a structure parameter of the structure by weighting a plurality of the index values with a weighting coefficient determined in accordance with the diagnosis purpose and arithmetically operating the index values; and
a display unit that displays the image,
wherein the endoscope system is connected to an endoscope information management system having a data storage unit that stores endoscope information management data including the diagnosis purpose so as to mutually communicate with each other through a network, and
wherein the diagnosis purpose acquisition unit receives the endoscope information management data through the network, and acquires the diagnosis purpose by extracting the diagnosis purpose from the received endoscope information management data.

* * * * *